US010779783B2

(12) United States Patent
Ito et al.

(10) Patent No.: US 10,779,783 B2
(45) Date of Patent: Sep. 22, 2020

(54) OPERATION PANEL DISPLAY DEVICE FOR MEDICAL X-RAY PHOTOGRAPHY APPARATUS, MEDICAL X-RAY PHOTOGRAPHY APPARATUS, AND DISPLAY METHOD IN OPERATION PANEL DISPLAY DEVICE FOR MEDICAL X-RAY PHOTOGRAPHY APPARATUS

(71) Applicant: J. MORITA MANUFACTURING CORPORATION, Kyoto-shi, Kyoto (JP)

(72) Inventors: Yutaka Ito, Kyoto (JP); Yoshito Sugihara, Kyoto (JP); Shinya Yamamoto, Kyoto (JP); Susumu Kirimura, Kyoto (JP)

(73) Assignee: J. MORITA MANUFACTURING CORPORATION, Kyoto (JP)

( * ) Notice: Subject to any disclaimer, the term of this patent is extended or adjusted under 35 U.S.C. 154(b) by 124 days.

(21) Appl. No.: 15/782,861

(22) Filed: Oct. 13, 2017

(65) Prior Publication Data

US 2018/0103920 A1 Apr. 19, 2018

(30) Foreign Application Priority Data

Oct. 14, 2016 (JP) .................................. 2016-202778

(51) Int. Cl.
*A61B 6/00* (2006.01)
*A61B 6/14* (2006.01)
(Continued)

(52) U.S. Cl.
CPC .............. *A61B 6/463* (2013.01); *A61B 6/032* (2013.01); *A61B 6/14* (2013.01); *A61B 6/145* (2013.01);
(Continued)

(58) Field of Classification Search
CPC ........... A61B 6/463; A61B 6/032; A61B 6/14; A61B 6/145; A61B 6/46; A61B 6/469; A61B 6/501; A61B 6/54
(Continued)

(56) References Cited

U.S. PATENT DOCUMENTS 5,692,027 A * 11/1997 Yoshimura ............... A61B 6/14
378/116
6,619,839 B2 9/2003 Yoshimura
(Continued)

FOREIGN PATENT DOCUMENTS

DE 10255958 A1 6/2004
JP H07-327985 A 12/1995
(Continued)

OTHER PUBLICATIONS

The Search Report from the corresponding European Patent Application No. 17 196 454.7 dated Apr. 6, 2018.
(Continued)

*Primary Examiner* — Taeho Jo
(74) *Attorney, Agent, or Firm* — Shinjyu Global IP

(57) ABSTRACT

A display device for a medical X-ray photography apparatus may include: a display panel including a photography mode selection region where a plurality of photography mode selection images corresponding to a plurality of X-ray photography modes are displayed; an interface that receives a selection operation to select one of the photography mode selection images displayed on the display panel; a processor that performs display processing of the selected photography mode selection image displayed on the display panel in response to the selection operation received through the interface; and an illustration display region included in the display panel where an illustration corresponding to the selected photography mode selection image is displayed.
(Continued)

When the selection operation is received, the selected photography mode selection image is displayed in a visually distinguishable manner, and the illustration corresponding to the selected photography mode is displayed in the illustration display region.

23 Claims, 21 Drawing Sheets

(51) Int. Cl.
  *A61B 6/04*   (2006.01)
  *A61B 6/03*   (2006.01)
(52) U.S. Cl.
  CPC ............. *A61B 6/46* (2013.01); *A61B 6/469* (2013.01); *A61B 6/501* (2013.01); *A61B 6/54* (2013.01)
(58) Field of Classification Search
  USPC ........................................................ 378/38
  See application file for complete search history.

(56) References Cited

U.S. PATENT DOCUMENTS

| | | | |
|---|---|---|---|
| 9,036,775 | B2 | 5/2015 | Yoshikawa et al. |
| 2007/0058786 | A1* | 3/2007 | Michael ............... A61B 6/505 378/207 |
| 2007/0237292 | A1* | 10/2007 | Malucelli ............. A61B 6/14 378/38 |
| 2007/0269002 | A1* | 11/2007 | Mazuir ................. H05G 1/54 378/38 |
| 2008/0002808 | A1* | 1/2008 | De Godzinsky ...... A61B 6/08 378/38 |
| 2013/0077746 | A1 | 3/2013 | Tsuji |
| 2013/0252196 | A1 | 9/2013 | Rasche et al. |
| 2014/0126686 | A1* | 5/2014 | Sadakane ............ A61B 6/06 378/13 |
| 2014/0126687 | A1* | 5/2014 | Yoshikawa .......... A61B 6/035 378/16 |
| 2014/0254745 | A1* | 9/2014 | Nakai ................. A61B 6/025 378/4 |
| 2014/0270082 | A1 | 9/2014 | Moellmer et al. |
| 2014/0328446 | A1* | 11/2014 | Sugihara ............ A61B 6/032 378/4 |

FOREIGN PATENT DOCUMENTS

| | | |
|---|---|---|
| JP | 2002-315746 A | 10/2002 |
| JP | 2012-110557 A | 6/2012 |
| JP | 5709820 B2 | 4/2015 |
| JP | 2016-002356 A | 1/2016 |
| JP | 2016-007338 A | 1/2016 |

OTHER PUBLICATIONS

The Office Action from the corresponding European Patent Application No. 17 196 454.7 dated Oct. 1, 2019.

\* cited by examiner

F I G. 5
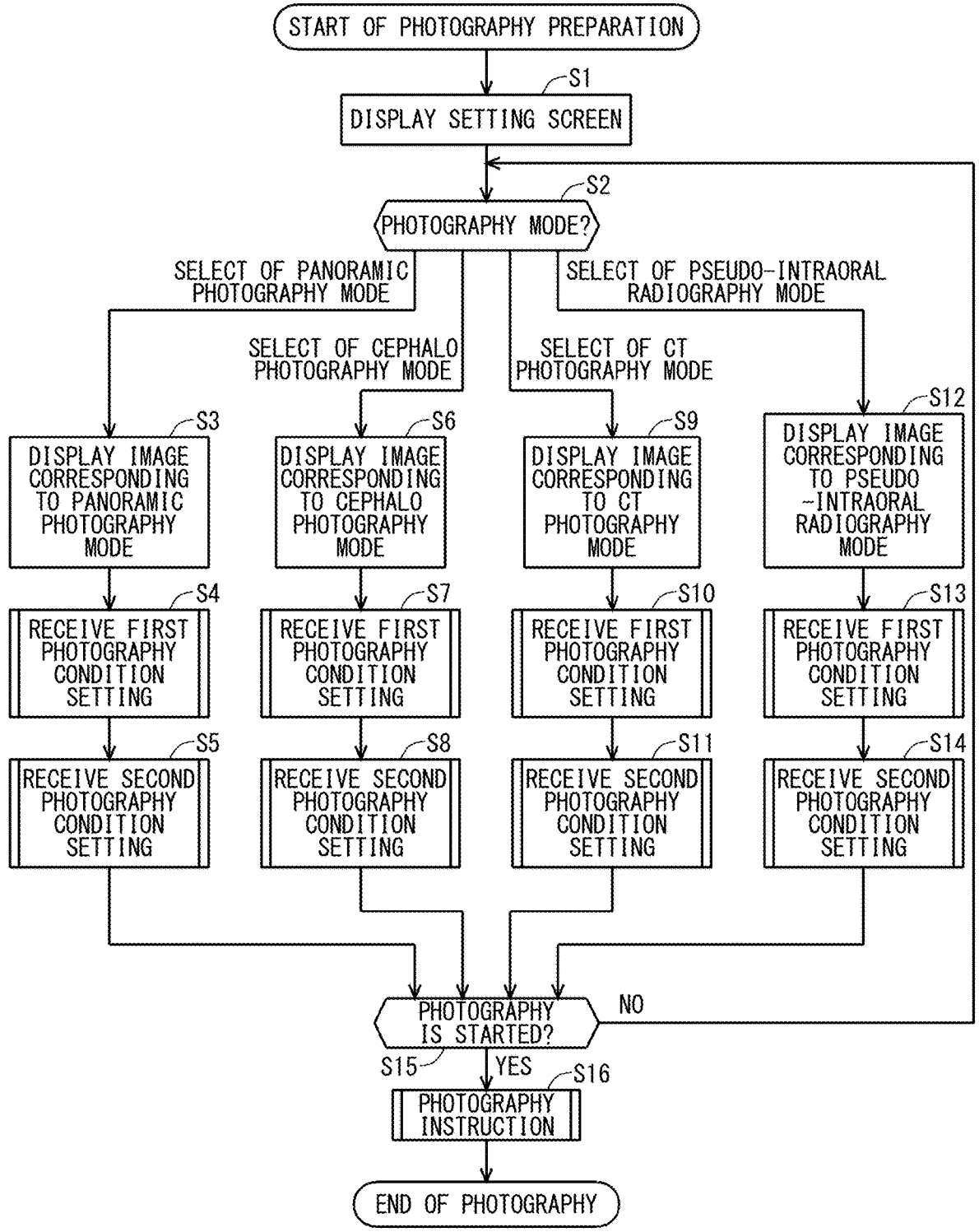

F I G. 3 6
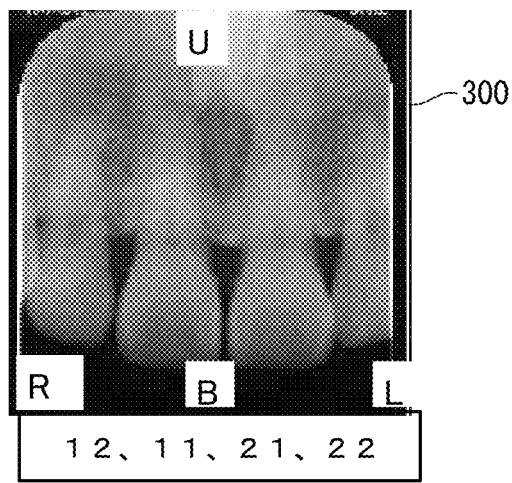

OPERATION PANEL DISPLAY DEVICE FOR MEDICAL X-RAY PHOTOGRAPHY APPARATUS, MEDICAL X-RAY PHOTOGRAPHY APPARATUS, AND DISPLAY METHOD IN OPERATION PANEL DISPLAY DEVICE FOR MEDICAL X-RAY PHOTOGRAPHY APPARATUS

TECHNICAL FIELD

Implementations may relate to a technology of displaying information about an operated content in an operation panel display device for medical X-ray photography apparatus.

BACKGROUND

Certain panel display devices may disclose a configuration including display means constructed with a liquid crystal display element or the like and input means overlapped on the display means as an operation panel for an X-ray photography device. The input means includes a "panorama" key, a "linear scan" key, and a "cephalo" key, and is provided independently of a photography mode display region of a display unit. When one of the "panorama" key, the "linear scan" key, and the "cephalo" key is operated, a photography mode is displayed in the photography mode display region according to the operation.

A touch panel may be used as an operation unit of the X-ray photography device.

During CT photography, a screen (such as an illustration image and a panoramic image) indicating a part or whole of a living body is displayed on a display unit, and an operator designates a region to be photographed using an operation panel or an operation unit, thereby designating the photography region.

A configuration in which a schematic diagram of a subject, a photography condition, and the like may be displayed on the display means.

A photography region setting screen may be used to set a photography region.

However, the photography mode display region of the display unit is provided independently of the "panorama" key, the "linear scan" key, and the "cephalo" key. For this reason, during or after the operation of one of the "panorama" key, the "linear scan" key, and the "cephalo" key, it is difficult to recognize which one of the photography modes is selected.

A configuration solving such a problem is not disclosed in the prior art.

An object of certain implementations is to easily perform the setting of the photography mode and the setting of the photography region.

SUMMARY

According to a first aspect of the present invention, an operation panel display device for a medical X-ray photography apparatus, the operation panel display device may comprise: a display panel including a photography mode selection region where a plurality of photography mode selection images corresponding to a plurality of X-ray photography modes are displayed; an operation receiver that receives a selection operation to select one of the photography mode selection images displayed on the display panel; a processor that performs display processing of the selected photography mode selection image displayed on the display panel in response to the selection operation received through the operation receiver; and an illustration display region included in the display panel where an illustration image corresponding to the selected photography mode selection image is displayed. When the selection operation is received, the selected photography mode selection image may be displayed on the display panel is displayed in a visually distinguishable manner in the photography mode selection region, and the illustration image corresponding to the selected photography mode selection image may be displayed in the illustration display region.

When a user operates one of the plurality of photography mode selection images, the operation receiver receives the user's selection operation, the one photography mode selection image of the plurality of photography mode selection images may be displayed in the visually distinguishable manner in the photography mode selection region according to the selection operation, and the illustration image corresponding to the selection operation is displayed in the illustration display region. Therefore, the user can easily recognize the selected photography mode before and after the selection operation, and easily sets the photography mode. For example, after the selection operation, the user can easily set the photography region in the display panel using the illustration image, which is displayed according to the selection operation.

According to a second aspect of the present invention, in the operation panel display device for a medical X-ray photography apparatus, the plurality of photography mode selection images may include at least two of: a panoramic photography mode selection image corresponding to panoramic photography, a cephalo photography mode selection image corresponding to cephalo photography, a CT photography mode selection image corresponding to CT photography, and a pseudo-intraoral radiography mode selection image corresponding to pseudo-intraoral radiograph.

Accordingly, the photography mode and the photography region can easily be set in selecting at least two of the panoramic photography, the cephalo photography, the CT photography, and the pseudo-intraoral radiography.

According to a third aspect of the present invention, in the operation panel display device for a medical X-ray photography apparatus, an illustration image may indicate an entire chin panorama or a plan view of a dental arch may be displayed in the illustration display region as an illustration image corresponding to a panoramic photography mode as said illustration image.

Accordingly, when the panoramic photography mode is selected, the illustration image indicating the entire chin panorama or the plan view of dental arch is displayed in the illustration display region. Therefore, the user can easily set the photography region using the illustration image indicating the entire chin panorama or the plan view of dental arch.

According to a fourth aspect of the present invention, in the operation panel display device for a medical X-ray photography apparatus, an illustration image of an entire chin panorama may be displayed in the illustration display region as an illustration image corresponding to the panoramic photography mode, and when a photography region selection operation based on the illustration image of the entire chin panorama is received, a photography region of a selected partial panorama may be displayed in the visually distinguishable manner in the illustration image of the entire chin panorama.

Accordingly, when the panoramic photography mode is selected, the illustration image indicating the entire chin panorama is displayed in the illustration display region. Therefore, the user can easily set the photography region using the illustration image of the entire chin panorama. Additionally, the selected photography region is displayed in the visually distinguishable manner in the illustration image of the entire chin panorama, so that the user can more easily set the photography region while recognizing the selected photography region.

According to a fifth aspect of the present invention, in the operation panel display device for a medical X-ray photography apparatus, an illustration image may indicate a front view or a side view of an external head shape may be displayed in the illustration display region as the illustration image corresponding to a cephalo photography mode.

Accordingly, when the cephalo photography mode is selected, the illustration image indicating the front view or side view of the external head shape is displayed in the illustration display region. Therefore, the user can easily set the photography region using the illustration image indicating the front view or side view of the external head shape.

According to a sixth aspect of the present invention, in the operation panel display device for a medical X-ray photography apparatus, the illustration image may indicate the front view or the side view of the external head shape may be divided into a plurality of regions while being able to be divided as a partial cephalo photography region, and when a selection operation for one of the plurality of regions is received, a selected photography region may be displayed in the visually distinguishable manner in the illustration image indicating the front view or the side view of the external head shape.

Accordingly, the user can easily designate the partial cephalo photography region.

According to a seventh aspect of the present invention, in the operation panel display device for a medical X-ray photography apparatus, an illustration image may indicate a plan view of a dental arch may be displayed in the illustration display region as an illustration image corresponding to a CT photography mode as said illustration image.

Accordingly, when the CT photography mode is selected, the illustration image indicating the plan view of the dental arch is displayed in the illustration display region. Therefore, the user can easily set the photography region using the illustration image indicating the plan view of the dental arch.

According to an eighth aspect of the present invention, in the operation panel display device for a medical X-ray photography apparatus, an illustration image of the entire chin panorama may be displayed in the illustration display region as an illustration image corresponding to a pseudo-intraoral radiography mode as said illustration image, and when a photography region selection operation based on the illustration image of the entire chin panorama is received, a selected photography region may be displayed in the visually distinguishable manner in the illustration image of the entire chin panorama.

Accordingly, when the pseudo-intraoral radiography mode is selected, the illustration image indicating the entire chin panorama is displayed in the illustration display region. Therefore, the user can easily set the photography region using the illustration image indicating the entire chin panorama. Because the selected photography region is displayed in the visually distinguishable manner in the illustration image of the entire chin panorama, the user more easily sets the photography region while recognizing the selected photography region.

According to a ninth aspect of the present invention, in the operation panel display device for a medical X-ray photography apparatus, a dental formula image may be displayed in the illustration display region as an illustration image corresponding to a pseudo-intraoral radiography mode as said illustration image such that a photography region can be selected in each tooth number or each block including a plurality of tooth numbers, and when a photography region selection operation based on the dental formula image is received, a selected photography region may be displayed in a visually distinguishable manner in the dental formula image.

Accordingly, when the pseudo-intraoral radiography mode is selected, the dental formula image is displayed in the illustration display region such that the photography region can be selected in each tooth number or each block including the plurality of tooth numbers. Therefore, the user easily sets the photography region in each tooth number or each block including the plurality of tooth numbers using the dental formula image. Additionally, the selected photography region is displayed in the visually distinguishable manner in the dental formula image, so that the user can more easily set the photography region while recognizing the selected photography region.

According to a tenth aspect of the present invention, in the operation panel display device for a medical X-ray photography apparatus, the display panel may include a first photography condition setting region where a photography condition setting image corresponding to the plurality of X-ray photography modes is displayed, and when a selection operation is received with respect to one of the plurality of photography mode selection images, the photography condition setting image corresponding to the selection operation may be displayed in the first photography condition setting region.

Accordingly, because the photography condition setting image corresponding to the photography mode selection operation is displayed, the user can easily set the detailed photography condition according to the photography mode.

According to an eleventh aspect of the present invention, in the operation panel display device for a medical X-ray photography apparatus, an image may indicate a patient size or an image indicating a chin shape may be displayed in the first photography condition setting region as the photography condition setting image corresponding to a panoramic photography mode.

Accordingly, when the panoramic photography mode is selected, at least one of the image indicating the patient size and the image indicating the chin shape that is of the photographing object is displayed in the first photography region setting region, so that the user can easily set the detailed photography region of the panoramic photography mode.

According to a twelfth aspect of the present invention, in the operation panel display device for a medical X-ray photography apparatus, a patient dental arch shape selection image may be displayed in the first photography condition setting region as the photography condition setting image corresponding to a panoramic photography mode, and when a selection operation for the patient dental arch shape selection image is received, a standard dental arch illustration image indicating a standard dental arch and a protraction dental arch illustration image indicating a protraction dental arch may be displayed in the display panel.

Accordingly, because the patient dental arch shape selection image is displayed in the first photography condition setting region as the photography condition setting image corresponding to the panoramic photography mode, the standard dental arch illustration image indicating the standard dental arch and the protraction dental arch illustration image indicating the protraction dental arch is displayed in the display panel when the user selects the patient dental arch shape selection image. The user can easily change the dental arch shape when performing the selection operation for the standard dental arch illustration image or the protraction dental arch illustration image indicating the protraction dental arch.

According to a thirteenth aspect of the present invention, in the operation panel display device for a medical X-ray photography apparatus, a CT photography region size selection image as the photography condition setting image corresponding to the CT photography mode may be displayed in the first photography condition setting region, and when a selection operation for the CT photography region size selection image is received, a plurality of CT photography region size candidate images may indicate CT photography region sizes different from each other may be displayed in the display panel.

Accordingly, because the CT photography region size selection image is displayed in the first photography condition setting region as the photography condition setting image corresponding to the CT photography mode, the plurality of CT photography region size candidate images indicating the CT photography region sizes different from each other are displayed in the display panel when the user selects the CT photography region size selection image. The user can easily change the CT photography region size when performing the selection operation for the plurality of CT photography region size candidate images.

According to a fourteenth aspect of the present invention, in the operation panel display device for a medical X-ray photography apparatus, a photography region setting image may be displayed in the first photography condition setting region as the photography condition setting image corresponding to a CT photography mode in order to select and designate a mode of CT photography region including a local CT photography mode, and when a selection of the local CT photography mode is received, a local CT illustration image indicating a size of a local CT photography region may be displayed as the photography condition setting image.

Accordingly, when the local CT photography mode is selected, the local CT illustration image indicating the size of the local CT photography region as the mode selection image is displayed, so that the user can easily recognize the size of the local CT photography region while performing the CT photography.

According to a fifteenth aspect of the present invention, in the operation panel display device for a medical X-ray photography apparatus, when the selection of the local CT photography mode is received, a region setting illustration image in which a circular shape indicating the local CT photography region is superposed on an illustration image of a plan view of a dental arch may be displayed as said illustration image in the illustration display region, and when relative movement of the circular shape indicating the local CT photography region with respect to the illustration image of the plan view of the dental arch is received, a position of the circular shape indicating the local CT photography region may be changed with respect to the illustration image of the plan view of the dental arch according to the relative movement.

Accordingly, the user can easily change the region where the local CT photography is performed while confirming the position of the circular shape indicating the local CT photography region in the illustration image of the plan view of the dental arch.

According to a sixteenth aspect of the present invention, in the operation panel display device for a medical X-ray photography apparatus, the dental formula image may be displayed in the illustration display region as the illustration image corresponding to the local CT photography mode such that a photography region can be selected in each tooth number or each block including a plurality of tooth numbers, and when photography region selection operation based on the dental formula image is received, a selected photography region may be displayed in the visually distinguishable manner in the dental formula image.

Accordingly, when the local CT photography mode is selected, the dental formula image is displayed in the illustration display region such that the photography region can be selected in each tooth number or each block including the plurality of tooth numbers. Therefore, the user easily sets the photography region in each tooth number or each block including the plurality of tooth numbers using the dental formula image. Additionally, the selected photography region is displayed in the visually distinguishable manner in the dental formula image, so that the user can more easily set the photography region while recognizing the selected photography region.

According to a seventeenth aspect of the present invention, in the operation panel display device for a medical X-ray photography apparatus, a photography region selection image may be displayed in the first photography condition setting region as the photography condition setting image corresponding to the cephalo photography mode, and when selection operation for the photography region selection image is received, a head front external form illustration image indicating a head front external form and a head side illustration image indicating a head side external form may be displayed in the display panel.

Accordingly, because the photography region selection image is displayed in the first photography condition setting region as the photography condition setting image corresponding to the cephalo photography mode, the head front external form illustration candidate image indicating the head front external form and the head side illustration candidate image indicating the head side external form are displayed in the display panel when the user selects the photography region selection image. Therefore, the user easily sets the photography region.

According to an eighteenth aspect of the present invention, in the operation panel display device for a medical X-ray photography apparatus, a patient size selection image may be displayed in the first photography condition setting region, and when selection operation for the patient size selection image is received, a plurality of patient size display illustration images indicating upper body external forms having different sizes may be display in the display panel.

Accordingly, the user performs the operation to select the plurality of patient size display illustration images, which allows the user to easily set the patient size.

According to a nineteenth aspect of the present invention, in the operation panel display device for a medical X-ray photography apparatus, the display panel may include a second photography condition setting region where a photography condition setting image corresponding to the plurality of X-ray photography modes is displayed, and when one of a panoramic photography mode, a CT photography mode, and a cephalo photography mode is received by selection operation for one of the plurality of photography mode selection images, a tube current setting image including tube current display and a tube voltage setting image including tube voltage display may be displayed in the second photography condition setting region, and a tube current or tube voltage adjustment image may be displayed by selection operation for the tube current setting image or the tube voltage setting image.

Accordingly, the user can easily adjust the tube current and the tube voltage while easily recognizing the tube current and the tube voltage.

According to a twentieth aspect of the present invention, in the operation panel display device for a medical X-ray photography apparatus, an X-ray image photographed in one of the plurality of X-ray photography modes may be displayed in the display panel while a symbol indicating one of an up, a down, a right, and or a left direction is superposed on the X-ray image.

Accordingly, the user can easily understand an orientation of the X-ray image.

According to a twenty-first aspect of the present invention, a medical X-ray photography apparatus includes the operation panel display device for medical X-ray photography apparatus.

Accordingly, the medical X-ray photography apparatus in which the photography mode and the photography region are easily set can be obtained.

According to a twenty-second aspect of the present invention, a display method in an operation panel display device for medical X-ray photography apparatus, the display method may include the steps of: (a) displaying a plurality of photography mode selection images corresponding to a plurality of X-ray photography modes in a photography mode selection region; (b) receiving selection operation for one of the plurality of photography mode selection images; (c) displaying one photography mode selection image in the plurality of photography mode selection images in a visually distinguishable manner in the photography mode selection region according to the selection operation when the selection operation in step (b) is received; and (d) displaying an illustration image in an illustration display region according to the selection operation when the selection operation in step (b) is received.

Accordingly, when the user operates one of the plurality of photography mode selection images, the user's selection operation is received, the one photography mode selection image of the plurality of photography mode selection images is displayed in the visually distinguishable manner in the photography mode selection region according to the selection operation, and the illustration image is displayed in the illustration display region according to the selection operation. Therefore, the user easily recognizes the selected photography mode before and after the selection operation, and easily sets the photography mode. For example, after the selection operation, the user can easily set the photography region in the display panel using the illustration image, which is displayed according to the selection operation.

According to a twenty-third aspect of the present invention, in the display method in the operation panel display device for medical X-ray photography apparatus, wherein at least two of a panoramic photography mode selection image corresponding to panoramic photography, a cephalo photography mode selection image corresponding to cephalo photography, a CT photography mode selection image corresponding to CT photography, and a pseudo-intraoral radiography mode selection image corresponding to pseudo-intraoral radiograph may be displayed as the plurality of photography mode selection images in step (a).

Accordingly, the photography mode and the photography region can easily be set in selecting at least two of the panoramic photography, the cephalo photography, the CT photography, and the pseudo-intraoral radiography.

According to a twenty-fourth aspect of the present invention, the display method in the operation panel display device for medical X-ray photography apparatus may further include the step of (e) displaying a photography condition setting image in a first photography condition setting region according to the selection operation when the selection operation in step (b) is received.

Accordingly, because the photography condition setting image is displayed according to the photography mode selection operation, the user can easily set the detailed photography condition according to the photography mode.

According to a twenty-fifth aspect of the present invention, the display method in the operation panel display device for medical X-ray photography apparatus may further include the step of (f) when one of a panoramic photography mode, a CT photography mode, and a cephalo photography mode is received by the selection operation in step (b), displaying a tube current setting image including tube current display and a tube voltage setting image including tube voltage display in a second photography condition setting region, and displaying a tube current or tube voltage adjustment image by selection operation for the tube current setting image or the tube voltage setting image.

Accordingly, the user can easily adjust the tube current and the tube voltage while easily recognizing the tube current and the tube voltage.

These and other objects, features, aspects and advantages of the present invention will become more apparent from the following detailed description of the present invention when taken in conjunction with the accompanying drawings.

BRIEF DESCRIPTION OF THE DRAWINGS

FIG. 5 is a flowchart illustrating entire display processing;

FIG. 36 is a view illustrating a display example of a photographed X-ray image.

DETAILED DESCRIPTION

Hereinafter, a medical X-ray photography apparatus and an operation panel display device according to a preferred embodiment will be described. An example in which the operation panel display device is integrally incorporated in the medical X-ray photography apparatus will be described. However, the operation panel display device can be provided independently of another part of the medical X-ray photography apparatus.

Figure 1:
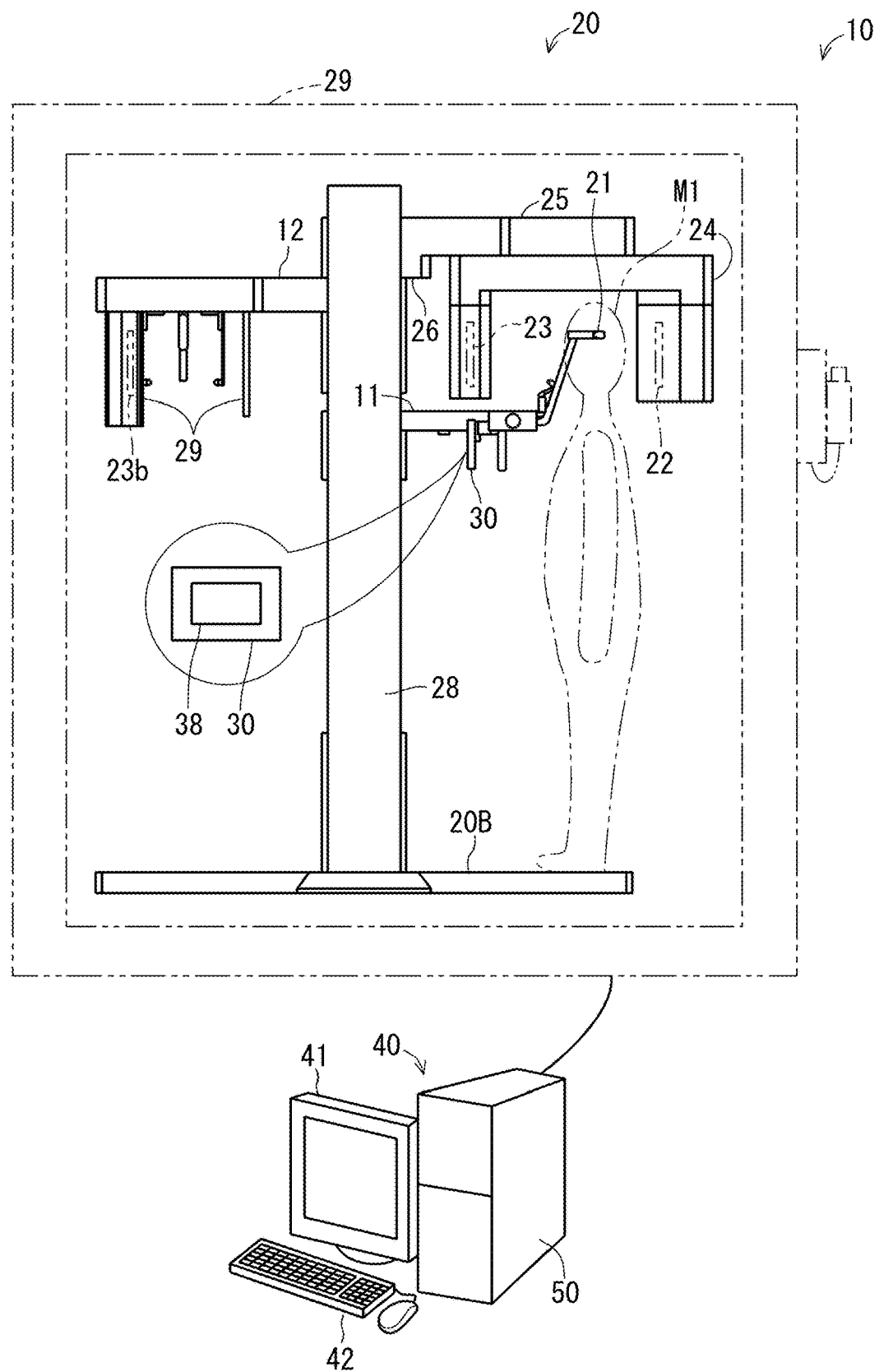
FIG. 1 is a schematic diagram illustrating an entire configuration of a medical X-ray photography apparatus.

FIG. 1 is a schematic diagram illustrating an entire configuration of a medical X-ray photography apparatus 10. The medical X-ray photography apparatus 10 includes a photographing main body 20 and an X-ray image processing device 40. The photographing main body 20 performs X-ray photography (in this case, X-ray CT photography) to collect projection data. The X-ray image processing device 40 generates various images by processing the projection data collected with the photographing main body 20. An example in which the operation panel display device is incorporated in the photographing main body 20 will be described in the preferred embodiment. The medical X-ray photography apparatus 10 is configured to be able to perform plural kinds of X-ray photography. At this point, the medical X-ray photography apparatus 10 is configured to be able to perform panoramic photography, cephalo photography, CT (Computed Tomography) photography, and pseudo-intraoral radiograph.

More specifically, the photographing main body 20 includes a post 28, an elevating unit 26, a turning-arm hanging arm 25, a U-shape turning arm 24, an X-ray generator 22 and an X-ray detector 23, a head fixing device 21, a cephalo photography head fixing device 29, and a main body controller 30. The post 28 is supported by a base 20B. The elevating unit 26 is elevatably provided on the post 28. The turning-arm hanging arm 25 is supported so as to extend horizontally above the elevating unit 26. The U-shape turning arm 24 is rotatably supported below a leading end of the turning-arm hanging arm 25 in a posture, in which the U-shape turning arm 24 is opened downward about a rotation axis along a gravity direction while a bracket or the like is interposed between the U-shape turning arm 24 and the turning-arm hanging arm 25. The X-ray generator 22 and the X-ray detector 23 are provided opposite each other at both ends of the turning arm 24. The head fixing device 21 is disposed between the X-ray generator 22 and the X-ray detector 23, and fixed to a head fixing device arm 11 extending horizontally from the post 28. The head fixing device 21 is used in the panoramic photography, the CT photography and so on. The cephalo photography head fixing device 29 is hung from a cephalo photography head fixing device hanging arm 12, which extends horizontally from the post 28 toward an opposite side to the turning-arm hanging arm 25. The main body controller 30 including an operation panel 38 is supported by the head fixing device arm 11. In FIG. 1, the operation panel 38 of the main body controller 30 is enlarged in a balloon.

The X-ray generator 22 can emit an X-ray beam constructed with a bundle of X-ray toward a head of a subject M1 fixed to the head fixing device 21. The X-ray detector 23 can detect the X-ray, which is emitted from the X-ray generator 22 and transmitted through the head of the subject M1. A cephalo photography X-ray detector 23b is incorporated in the cephalo photography head fixing device 29.

The turning arm 24 has a U-shape opened downward. At both the ends of the turning arm 24, the X-ray generator 22 and the X-ray detector 23 are supported opposite each other. The post 28 is vertically provided so as to extend along the gravity direction (vertical direction), and the elevating unit 26 is elevatably supported at an upper end of the post 28. The elevating unit 26 projects toward one side with respect to the post 28. The turning arm 24 is rotatably supported about a turning axis extending along the gravity direction while hung from the leading end of the turning-arm hanging arm 25. The turning arm 24 is elevated when the elevating unit 26 is elevated. A rotary drive part, such as a motor, which rotates the turning arm 24, is incorporated in the leading end of the turning-arm hanging arm 25, and the turning arm 24 is rotated by the rotation of the rotary drive part.

While the head of the subject M1 is being fixed using the head fixing devices 21 located between both the ends of the turning arm 24, the X-ray photography is performed with the turning arm 24 stopped or rotated according to the desired photography mode. Therefore, X-ray image data necessary for the generation of a panoramic photography image, a cephalo photography image, a CT photography image, and a pseudo-intraoral radiograph image can be obtained. For example, the X-ray photography is performed while the turning arm 24 is rotated within a given range, which allows the obtainment of the panoramic photography image. For example, the head of the subject M1 is fixed to the cephalo photography head fixing device 29 hung from the cephalo photography head fixing device hanging arm 12 extending horizontally from the post 28 while the turning arm 24 is stopped, and the X-ray generator 22 emits the X-ray to perform the X-ray photography, which allows the obtainment of the cephalo photography image. For example, the X-ray photography is performed while the turning arm 24 is rotated, which allows the obtainment of X-ray CT image data necessary for the generation of the X-ray CT photography image. For example, the head of the subject M1 is being fixed using the head fixing device 21, and three-dimensional image data of the photographing object is obtained by the X-ray photography while the turning arm 24 is rotated, which allows the pseudo-intraoral radiograph image to be obtained from the three-dimensional image data. Sometimes a cephalo photography image photographing function, a pseudo-intraoral radiograph image photographing function or the like is eliminated. The operation panel display device of the preferred embodiment is suitable for a photography device that performs at least two of the panoramic photography image photographing function, the cephalo photography image photographing function, the CT photography image photographing function, and the pseudo-intraoral radiograph image photographing function.

The main body controller 30 can receive each instruction issued to the photographing main body 20, and control each motion of the photographing main body 20. The main body controller 30 is fixed to the arm, which extends horizontally from the post 28 and supports the head fixing device 21. The operation panel device 38 is provided in the main body controller 30 in order to display various pieces of information from the main body controller 30 and to receive various instructions to the main body controller 30. In the operation panel device 38 constructed with a touch panel, a touch detector is provided on a display screen of a display unit such as a liquid crystal display panel. In the operation panel device 38, touch operation performed on the display screen is detected with the touch detector, which allows the reception of operation for the medical X-ray photography apparatus 10. A display screen example of the touch panel device 38, a reception content example of the touch operation, and a display control example based on the touch operation will be described in detail later. A push button and so on may be provided near the operation panel device 38.

Each unit of the photographing main body 20 is accommodated in the X-ray protection chamber 29. A push button switch called a dead man switch that issues an X-ray irradiation instruction to the main body controller 30 is provided outside a wall of the X-ray protection chamber 29.

In the preferred embodiment, the X-ray generator 22 and the X-ray detector 23 are attached to both the ends of the U-shape turning arm 24. Alternatively, the X-ray generator and the X-ray detector may be supported opposite each other using an annular member. In the preferred embodiment, the X-ray generator 22 and the X-ray detector 23 are supported while being rotatable about the vertical axis. Alternatively, the X-ray generator and the X-ray detector may be supported while being rotatable about an axis along the horizontal direction orthogonal to the vertical direction or an axis along an inclined direction intersecting both the horizontal direction and the vertical direction.

The X-ray image processing device 40 includes an information processing main body 50 constructed with a computer or a workstation. The X-ray image processing device 40 can transmit and receive various pieces of data to and from the photographing main body 20 through a communication cable. The data can wirelessly be transmitted and received between the photographing main body 20 and the X-ray image processing device 40.

A display unit 41 constructed with a display device such as a liquid crystal monitor and an operation unit 42 constructed with a keyboard, a mouse, or the like are connected to the X-ray image processing device 40. Using the mouse or the like, an operator performs pointer operation on a character or an image displayed on the display unit 41, which allows an operator to issue various instructions to the information processing main body 50. The display unit 41 can also be constructed with the touch panel. In this case, the display unit 41 includes a part of or all the functions of the operation unit 42. The display unit 41 and the operation unit 42 may be used instead of the operation panel device 38. This enables cost reduction of the X-ray photography device. The X-ray image processing device 40 already purchased by the operator is used instead of the operation panel device 38, and an operation screen of the operation panel device 38 may be displayed on the display unit 41, or operated using the display unit including the touch panel.

<Block Diagram of Medical X-Ray Photography Apparatus>

Figure 2:
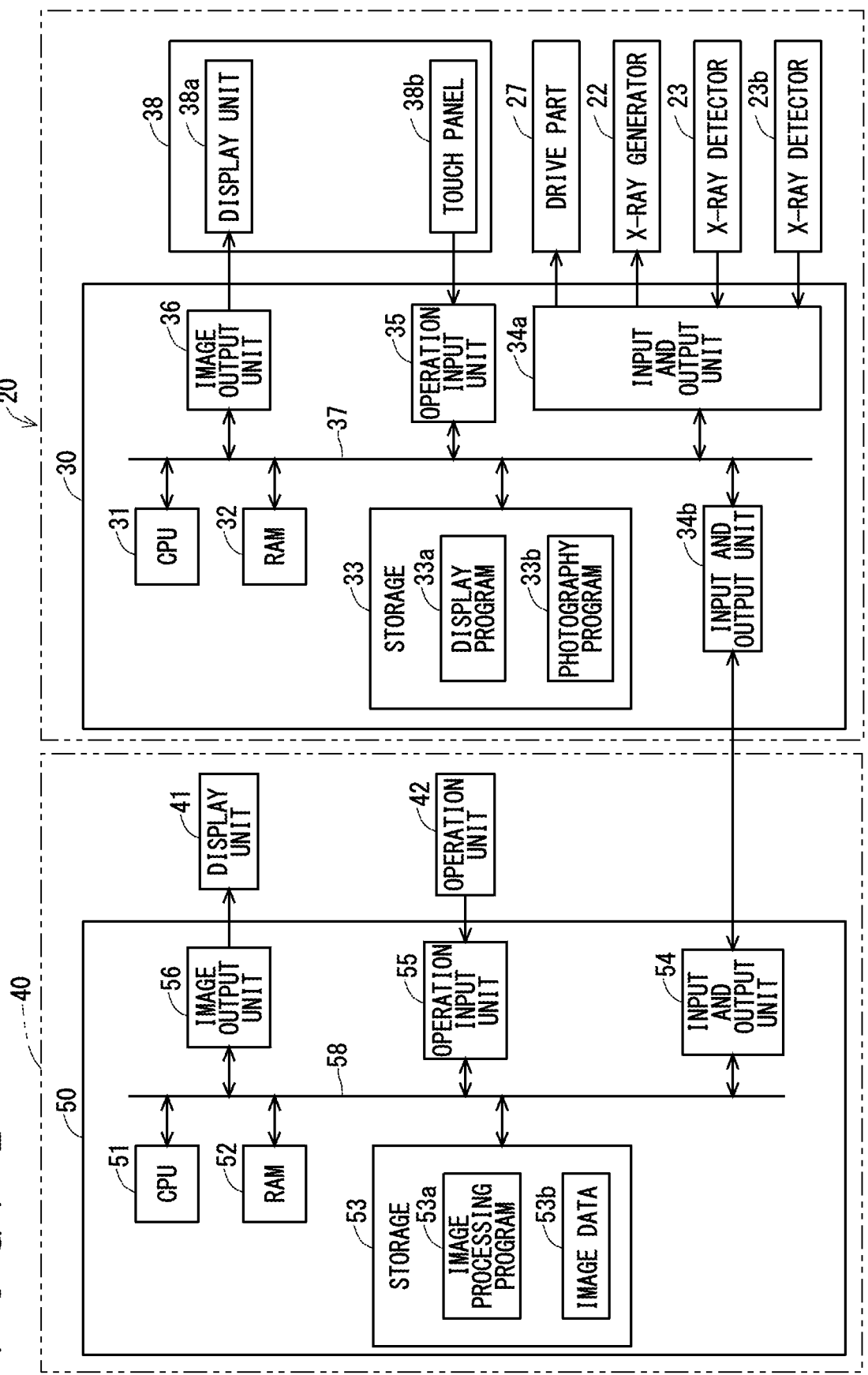
FIG. 2 is a block diagram illustrating an electric configuration of the medical X-ray photography apparatus.

FIG. 2 is a block diagram illustrating an electric configuration of the medical X-ray photography apparatus 10.

The main body controller 30 of the photographing main body 20 controls X-ray photography action of the photographing main body 20. The main body controller 30 is constructed with a general computer in which a CPU (Central Processing Unit) 31, a RAM (Random Access Memory) 32, a storage 33, input and output units 34a and 34b, an operation input unit 35, and an image output unit 36 are connected to one another through a bus line 37. The storage 33 is constructed with a nonvolatile storage device such as a flash memory and a hard disk drive. A display program 33a and a photography program 33b are stored in the storage 33. The display program 33a controls the display for a display unit 38a when the photographing main body 20 receives various instructions related to the X-ray photography. The photography program 33b is used when the photographing main body 20 performs the X-ray photography. The RAM 32 is used as a work area when the CPU 31 performs predetermined processing. The input and output unit 34a is connected to a motor (described as a drive part 27 in FIG. 2) that turns or elevates the turning arm 24 of the photographing main body 20, the X-ray generator 22, and the X-ray detectors 23 and 23b. The input and output unit 34b is connected to the X-ray image processing device 40. The operation input unit 35 is connected to a touch detector 38b, and the image output unit 36 is connected to the display unit 38a.

In the main body controller 30, the CPU 31 performs arithmetic processing in response to a procedure written in the display program 33a and the instruction received through the touch detector 38b, whereby the instructions related to the X-ray photography are received while the display for the display unit 38a is controlled. When the CPU 31 performs the arithmetic processing in response to the procedure written in the photography program 33b and the received instructions related to the X-ray photography, the drive part 27 and the X-ray generator 22 are driven, and detection results detected through the subject M1 with the X-ray detectors 23 and 23b can be obtained.

In the preferred embodiment, the main body controller 30 including the display unit 38a and the touch detector 38b is an example of the operation panel display device for medical X-ray photography apparatus. In this case, the display unit 38a corresponds to the display panel, and the touch detector 38b corresponds to the operation receiver.

The X-ray image processing device 40 generates an X-ray image data 53b based on photography data from the photographing main body 20. The information processing main body 50 is constructed with a general computer in which a CPU 51, a RAM 52, a storage 53, an input and output unit 54, an operation input unit 55, and an image output unit 56 are connected to one another through a bus line 58. The storage 53 is constructed with a nonvolatile storage device such as a flash memory or a hard disk drive. An image processing program 53a and an X-ray image data 53b are stored in the storage 53. Using the image processing program 53a, the information processing main body 50 generates the X-ray image data 53b based on the photography data from the photographing main body 20. Management data in which the X-ray image data 53b and specific information such as the subject M1 are corresponded to each other may be stored in the storage 53. The X-ray image processing device 40 may receive data related to the photography condition from the main body controller 30, and store the data related to the photography condition in the storage 53 while corresponding the data related to the photography condition to the generated X-ray image data 53b. The RAM 52 is used as a work area when the CPU 51 performs predetermined processing. The input and output unit 54 is connected to the photographing main body 20, and X-ray photography data obtained with the photographing main body 20 is input to the X-ray image processing device 40 through the input and output unit 54. The operation input unit 35 is connected to the operation unit 42, and the image output unit 56 is connected to the display unit 41.

In the information processing main body 50, the CPU 31 performs the arithmetic processing according to the image processing program 53a, thereby performing processing as an image processor that generates the desired X-ray image data based on the X-ray photography data obtained with the photographing main body 20. That is, pieces of data such as a panoramic photography image, a cephalo photography image, a CT photography image, and a pseudo-intraoral radiograph image are generated in response to the instruction received through the main body controller 30. The generated X-ray image data is stored in the storage 53.

Figure 3:
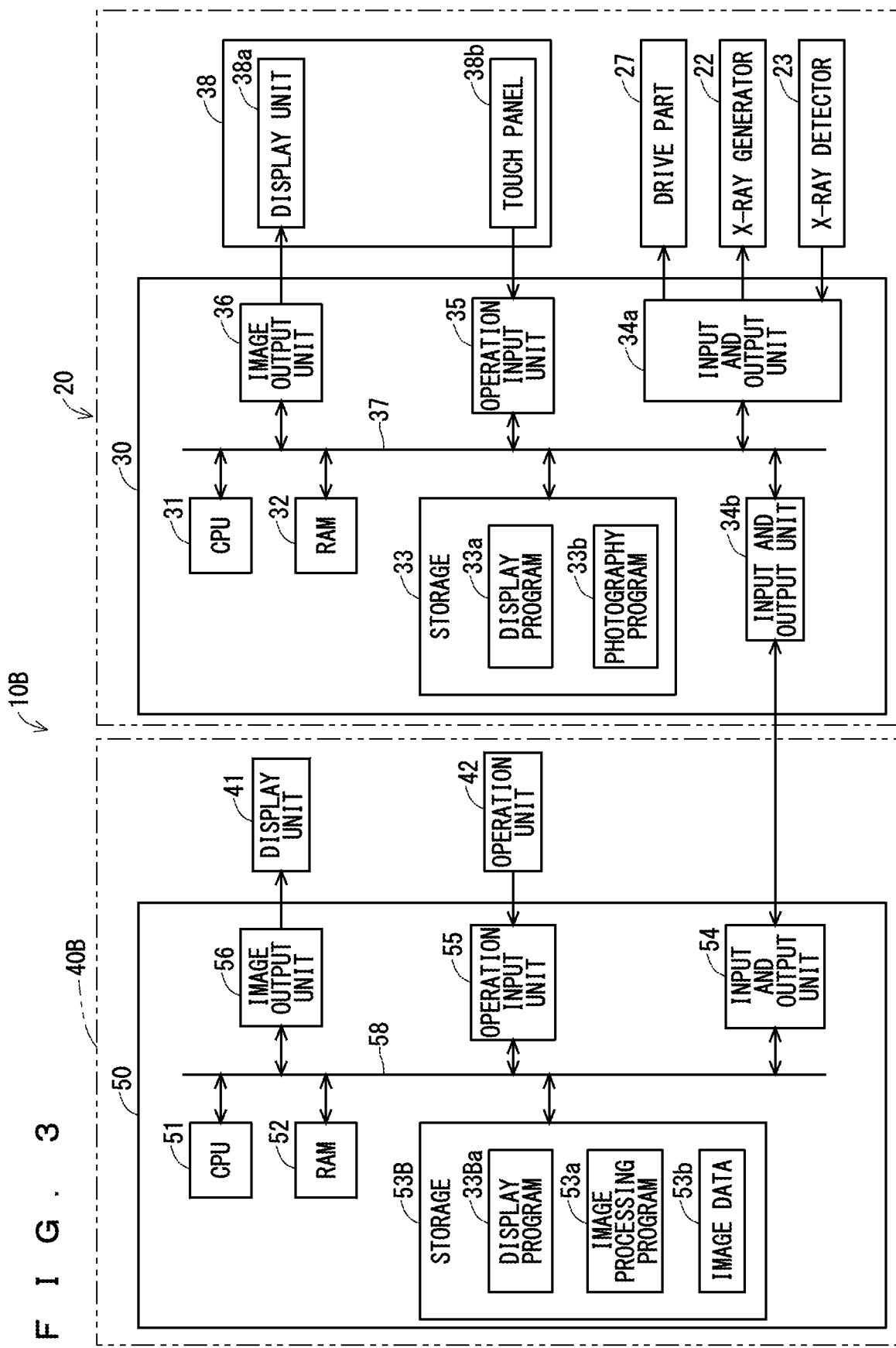
FIG. 3 is a block diagram illustrating an electric configuration of a medical X-ray photography apparatus according to a modification.

In the preferred embodiment, the display program 33a is stored in the storage 33 of the main body controller 30 of the photographing main body 20. As illustrated in FIG. 3, in a medical X-ray photography apparatus 10B according to a modification, a display program 33Ba may be stored in a storage 53B of an X-ray image processing device 40B similarly to the display program 33a. In this case, when the display unit is constructed with the touch panel, the touch operation performed on the display unit can be received similarly to the touch panel device 38. In the case that the display unit is constructed with not the touch panel but a simple display device such as a liquid crystal monitor, the operation performed on the image displayed on the display unit using a mouse can be received. In this case, the X-ray image processing device 40 including the display unit and the operation input unit such as the mouse is an example of the operation panel display device of the medical X-ray photography apparatus, the display unit corresponds to the display panel, and the operation input unit such as the mouse corresponds to the operation receiver.

The display program 33a or 33Ba is previously stored in the storage 33 or 53B. Alternatively, the display program 33a or 33Ba may be provided to the existing medical X-ray photography apparatus or the information processing main body that controls the existing medical X-ray photography apparatus in a form in which the display program 33a or 33Ba is recorded in a CD-ROM, a DVD-ROM, or an external recording medium such as a flash memory or by download of the display program 33a or 33Ba from an external server through a network. Alternatively, a part of or all the functions implemented in each unit may be implemented with a dedicated logic circuit in a hardware manner.

<Display Processing>
<Layout of Each Region in Display Image>

A layout of a display region 60 displayed on the display unit 38a will be described before a display processing example of the display unit 38a with the main body controller 30 is described. At this point, the description will be made based on an example of the image displayed on the display unit 38a. As described later, ac actual content displayed in each region is properly changed according to each photography mode. The display region 60 includes a photography mode selection region 62, an illustration display region 70, a first photography condition setting region 80, and a second photography condition setting region 90.

The photography mode selection region 62 is a region where photography mode selection images 63, 64, 65, and 66 corresponding to plural X-ray photography modes are displayed. In this case, the photography mode selection region 62 is set to an upper region of the display region 60. The photography mode selection region may be set to another place of the display region, for example, a left region.

More specifically, the photography mode selection region 62 includes the panoramic photography mode selection image 63 corresponding to the panoramic photography mode, the cephalo photography mode selection image 64 corresponding to the cephalo photography mode, the CT photography mode selection image 65 corresponding to the CT photography mode, and the pseudo-intraoral radiography mode selection image 66 corresponding to the pseudo-intraoral radiography mode.

The panoramic photography mode is a photography mode that is performed to obtain one image of a whole mouth (or a part of the mouth) along a tooth row. For example, in the panoramic photography mode, the X-ray photography is performed with the turning arm 24 rotated within a predetermined range. An image indicating characters "Pan" is displayed as the panoramic photography mode selection image 63.

The cephalo photography mode is a photography mode that is performed to take a roentgenographic cephalogram. For example, in the cephalo photography mode, the X-ray photography of the head is performed from a given direction while the rotation of the turning arm 24 is stopped. An image indicating characters "Ceph" is displayed as the cephalo photography mode selection image 64.

The CT photography mode is a photography mode that is performed to obtain a tomographic image of the whole tooth row (or a part of the tooth row). For example, in the CT photography mode, the X-ray photography is performed while the turning arm 24 is rotated. An image indicating characters "CT" is displayed as the CT photography mode selection image 65.

The pseudo-intraoral radiography mode is a photography mode in which photography similar to the conventional intraoral radiography is performed by extraoral radiography in which a photograph is taken while the X-ray detector is disposed outside the mouth. Specifically, for example, tomosynthesis photography is performed while the whole photography region is irradiated with the X-ray during the photographing, and the image similar to the conventional intraoral radiography is taken based on the photography data of the tomosynthesis photography. For example, in the pseudo-intraoral radiography mode, the X-ray photography is performed while the turning arm 24 is rotated within a predetermined range. An image indicating characters "TTS" (meaning Teeth Tomosynthesis) is displayed as the pseudo-intraoral radiography mode selection image 66.

The panoramic photography mode selection image 63, the cephalo photography mode selection image 64, the CT photography mode selection image 65, and the pseudo-intraoral radiography mode selection image 66 are horizontally arrayed from left to right in this order in the photography mode selection region 62. The images displayed as the photography mode selection images 63, 64, 65, and 66 are not limited to the examples in FIG. 4. For example, the images may be illustrations in which the photography modes are visualized.

In the preferred embodiment, the four selection images of the panoramic photography mode selection image 63, the cephalo photography mode selection image 64, the CT photography mode selection image 65, and the pseudo-intraoral radiography mode selection image 66 are displayed in the photography mode selection region 62. There is no limitation to the selection images displayed in the photography mode selection region 62. Preferably at least two of the panoramic photography mode selection image corresponding to the panoramic photography, the cephalo photography mode selection image corresponding to the cephalo photography, the CT photography mode selection image corresponding to the CT photography, and the pseudo-intraoral radiography mode selection image corresponding to the pseudo-intraoral radiograph are displayed as the plural photography mode selection images in the photography mode selection region 62.

Figure 4:
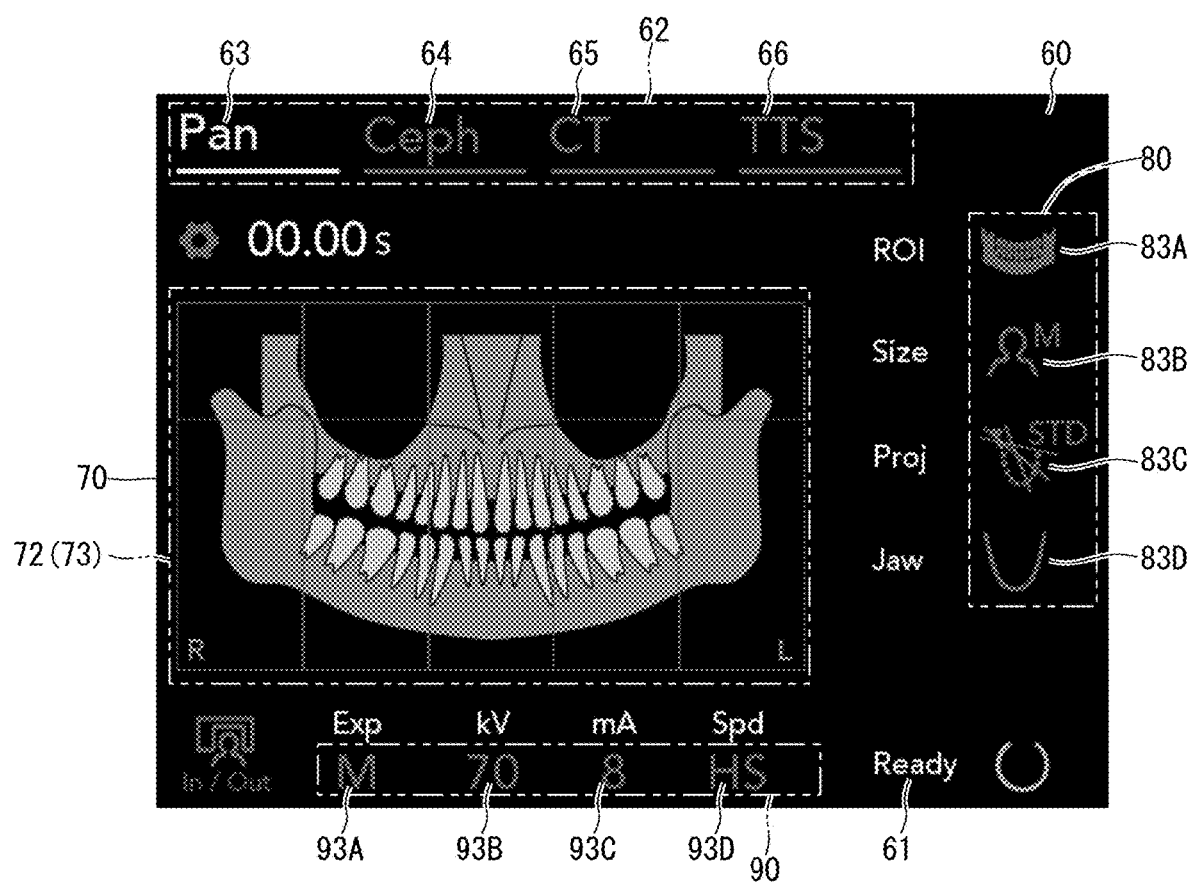
FIG. 4 is a view illustrating a display example when a panoramic photography mode selection image is selected.

The touch detector 38*b* of a two-dimensional position detector that detects a touch position in the display region 60 is provided on the display region 60 of the display unit 38*a*. When a user touches one of the photography mode selection images 63, 64, 65, and 66, the touch detector 38*b* receives the selection operation for one of the photography mode selection images 63, 64, 65, and 66. When the selection operation is received, one photography mode selection image is displayed according to the selection operation while visually distinguished from other photography region selection images. FIG. 4 illustrates the case that the panoramic photography mode selection image 63 is displayed in color (including different shade of color) different from the mode selection images 64, 65, and 66 while being distinguishable from the mode selection images 64, 65, and 66 while the other photography mode selection images 64, 65, and 66 remain in the display region 60 without completely disappearing. It is contemplated in some implementations that the other photography mode selection images 64, 65, and 66 may completely disappear from the display region 60.

The illustration display region 70 is a region where illustration images 72 corresponding to the plural X-ray photography modes are displayed. The illustration display region 70 is disposed in a vertically middle portion of the display region 60 and in the widest range. In the illustration display region 70, an illustration image 72 suitable to display the photography mode selection images 63, 64, 65, and 66 is displayed according to the selection operation for the photography mode selection images 63, 64, 65, and 66 of the photography mode selection region 62. FIG. 4 illustrates the illustration image 72 corresponding to the panoramic photography mode. The photography mode and the illustration image do not necessarily correspond to each other in a one-to-one manner. For example, the one photography mode may correspond to the plural illustration images. The illustration image similar to the illustration image corresponding to one photography mode may correspond to another photography mode. An example of the illustration image corresponding to each photography mode will be described later.

The first photography condition setting region 80 is a region where the photography condition setting images corresponding to the plural X-ray photography modes are displayed. The first photography condition setting region 80 is provided in a right portion of the display region 60. At this point, a region-of-interest setting image 83A, a patient size selection image 83B, a projection setting image 83C, and a dental arch shape selection image 83D are displayed as the photography condition setting image corresponding to the panoramic photography mode in the first photography condition setting region 80. In the preferred embodiment, the region-of-interest setting image 83A is an image in which a region-of-interest illustration image is added beside characters "ROI", the patient size selection image 83B is an image in which the illustration image indicating an upper half of the body and a character "M" indicating the size are added beside characters "Size", the projection setting image 83C is an image in which the illustration images indicating the dental arch and a projection method is added beside characters "Proj", and the dental arch shape selection image 83D is an image in which a dental arch shape is added beside characters "Jaw" or "Chin". That is, the first photography condition setting region 80 mainly includes images used to set the photography conditions related to the subject in photography conditions. As described later, even in the same photography mode, existence and content of the display of one of the photography condition setting images 83A, 83B, 83C, and 83D can be changed according to the setting operation for the other of the photography condition setting images 83A, 83B, 83C, and 83D.

The second photography condition setting region 90 is a region where the photography condition setting images corresponding to the plural X-ray photography modes are displayed. The second photography condition setting region 90 is provided in a lower portion of the display region 60. At this point, in the second photography condition setting region 90, an irradiation setting image 93A, a tube voltage setting image 93B, a tube current setting image 93C, and a photographing speed setting image 93D are displayed as the photography condition setting image corresponding to the panoramic photography mode. The irradiation setting image 93A is an image in which a character "M" indicating manual setting is added below characters "Exp", the tube voltage setting image 93B is an image in which a numerical character (in this case, "70") indicating a tube voltage setting value is added below characters "kV" indicating a unit of tube voltage, the tube current setting image 93C is an image in which a numerical character (in this case, "8") indicating a tube current setting value is added below characters "mA" indicating a unit of tube current, and the photographing speed setting image 93D is an image in which a setting state of speed (in this case, characters "HS" indicating High Speed) is added below characters "Spd" indicating the speed. That is, the second photography condition setting region 90 mainly includes images used to set photography device operating conditions such as an irradiation condition and an arm speed in the photography conditions. As described later, even in the same photography mode, the existence of the display of one of the photography condition setting images 93A, 93B, 93C, and 93D can be changed according to the setting operation for the other of the photography condition setting images 93A, 93B, 93C, and 93D.

<Entire Display Processing>

Entire display processing performed with the display unit 38a under the control of the main body controller 30 will be described with reference to FIG. 5.

After positioning the subject M1 with respect to the photographing main body 20, the user sets the photography mode and the photography condition using the touch panel device 38 including the display unit 38a and the touch detector 38b.

In step S1, the main body controller 30 displays a setting screen. The example in FIG. 4 is considered as the initially-displayed setting screen. A final screen in the last setting is also considered as the initially-displayed setting screen. That is, the plural photography mode selection images 63, 64, 65, and 66 corresponding to the plural X-ray photography modes are displayed in the photography mode selection region 62 (step (a)).

In step S2, the main body controller 30 receives the selection operation for one of the plural photography modes (step (b)). The user touches one of the photography mode selection images 63, 64, 65, and 66 displayed in the photography mode selection region 62, which allows the user to select the photography mode in which the photograph is taken. The touch detector 38b receives the user selection. In the case that any photography mode selection images 63, 64, 65, and 66 are not selected, the already-selected photography mode may continuously be selected.

The flow goes to step S3 when the panoramic photography mode is selected in step S2, the flow goes to step S6 when the cephalo photography mode is selected in step S2, the flow goes to step S9 when the CT photography mode is selected in step S2, and the flow goes to step S12 when the pseudo-intraoral radiography mode is selected in step S2.

In step S3, the image corresponding to the panoramic photography mode is displayed on the display unit 38a. For example, the image in FIG. 4 is displayed on the display unit 38a.

At this point, in the photography mode selection region 62 of the display unit 38a, one of the plural photography mode selection images 63, 64, 65, and 66 is displayed in the visually distinguishable manner according to the selection operation. In the example of FIG. 4, the panoramic photography mode selection image 63 is displayed in color (including different shade of color) different from the mode selection images 64, 65, and 66 while being distinguishable from the mode selection images 64, 65, and 66.

The illustration image is displayed in the illustration display region 70 of the display unit 38a according to the selection operation. For the example in FIG. 4, an entire jaw or chin panorama illustration image 73 in which the entire jaw or chin is viewed from a front is displayed as the illustration image 72 corresponding to the panoramic photography mode in the illustration display region 70.

A first photography condition setting image is displayed in the first photography condition setting region 80 of the display unit 38a according to the selection operation. For the example in FIG. 4, the region-of-interest setting image 83A, the patient size selection image 83B, the projection setting image 83C, and the dental arch shape selection image 83D are displayed in the first photography condition setting region 80.

A second photography condition setting image is displayed in the second photography condition setting region 90 of the display unit 38a according to the selection operation. For the example in FIG. 4, the irradiation setting image 93A, the tube voltage setting image 93B, the tube current setting image 93C, and the photographing speed setting image 93D are displayed in the second photography condition setting region 90.

In step S4, first photography condition setting is received using the region-of-interest setting image 83A, patient size selection image 83B, projection setting image 83C, and dental arch shape selection image 83D in the first photography condition setting region 80 displayed on the display unit 38a.

In step S5, second photography condition setting is received using the irradiation setting image 93A, tube voltage setting image 93B, tube current setting image 93C, and photographing speed setting image 93D in the second photography condition setting region 90 displayed on the display unit 38a.

Then, the flow goes to step S15.

The flow goes to step S6 when the cephalo photography mode is selected in step S2.

In step S6, the image corresponding to the cephalo photography mode is displayed on the display unit 38a.

In steps S7 and S8, the first photography condition setting and the second photography condition setting are received similarly to steps S4 and S5. Then the flow goes to step S15.

The flow goes to step S9 when the CT photography mode is selected in step S2.

In step S9, the image corresponding to the CT photography mode is displayed on the display unit 38a.

Then, in steps S10 and S11, the first photography condition setting and the second photography condition setting are received similarly to steps S4 and S5. Then, the flow goes to step S15.

The flow goes to step S12 when the pseudo-intraoral radiography mode is selected in step S2.

In step S12, the image corresponding to the pseudo-intraoral radiography mode is displayed on the display unit 38a.

In steps S13 and S14, the first photography condition setting and the second photography condition setting are received similarly to steps S4 and S5. Then the flow goes to step S15.

Image examples corresponding to the cephalo photography mode, the CT photography mode, and the pseudo-intraoral radiography mode in the illustration display region 70, image examples in the first photography condition setting region 80, and image examples in the second photography condition setting region 90 will be described later while the display screens are illustrated.

In step S15, the main body controller 30 determines whether a photography start instruction is issued. For example, the photography start instruction is issued when the user touches a key 61 (in this case, a region "READY" displayed in a bottom right) displayed in the display region 60 of the display unit 38a. When the photography start instruction is not issued in step S15, the flow returns to step S2, and the pieces of processing from step S2 are repeated. When the photography start instruction is issued in step S15, the flow goes to step S16. In step S16, according to the set photography mode and photography condition, the drive part 27, the X-ray generator 22, and the X-ray detector 23 are controlled to perform the photography. Therefore, the processing related to the photography mode setting and the photography condition setting is ended.

As described above, when the selection operation is received in step S2, the processing of displaying one of the plural photography mode selection images 63, 64, 65, and 66 in the visually distinguishable manner in the photography mode selection region 62 is performed in steps S3, S6, S9, and S12 (step (c)). When the selection operation is received in step S2, the processing of displaying the illustration image 72 in the illustration display region 70 is performed according to the selection operation (step (d)). When the selection operation is received in step S2, the processing of displaying the photography condition setting image (such as the region-of-interest setting image 83A, the patient size selection image 83B, the projection setting image 83C, and the dental arch shape image example 83D) in the first photography condition setting region 80 is performed according to the selection operation in steps S3, S6, S9, and S12 (step (e)).

<Display Processing in Panoramic Photography Mode>

A display processing example in the case that the panoramic photography mode is selected will be described more specifically.

As described above, the display image example of the display unit 38a in the case that the panoramic photography mode is selected includes the photography mode selection region 62, the illustration display region 70, the first photography condition setting region 80, and the second photography condition setting region 90.

In the photography mode selection region 62, the case that the panoramic photography mode selection image 63 is displayed in color (including different shade of color) different from the mode selection images 64, 65, and 66 while being distinguishable from the mode selection images 64, 65, and 66.

The illustration display region 70 is the region where the illustration images 72 corresponding to the plural X-ray photography modes are displayed. For the example in FIG. 4, the entire jaw or chin panorama illustration image 72 indicating the entire jaw or chin panorama is displayed as the illustration image corresponding to the panoramic photography mode in the illustration display region 70.

Figure 6:
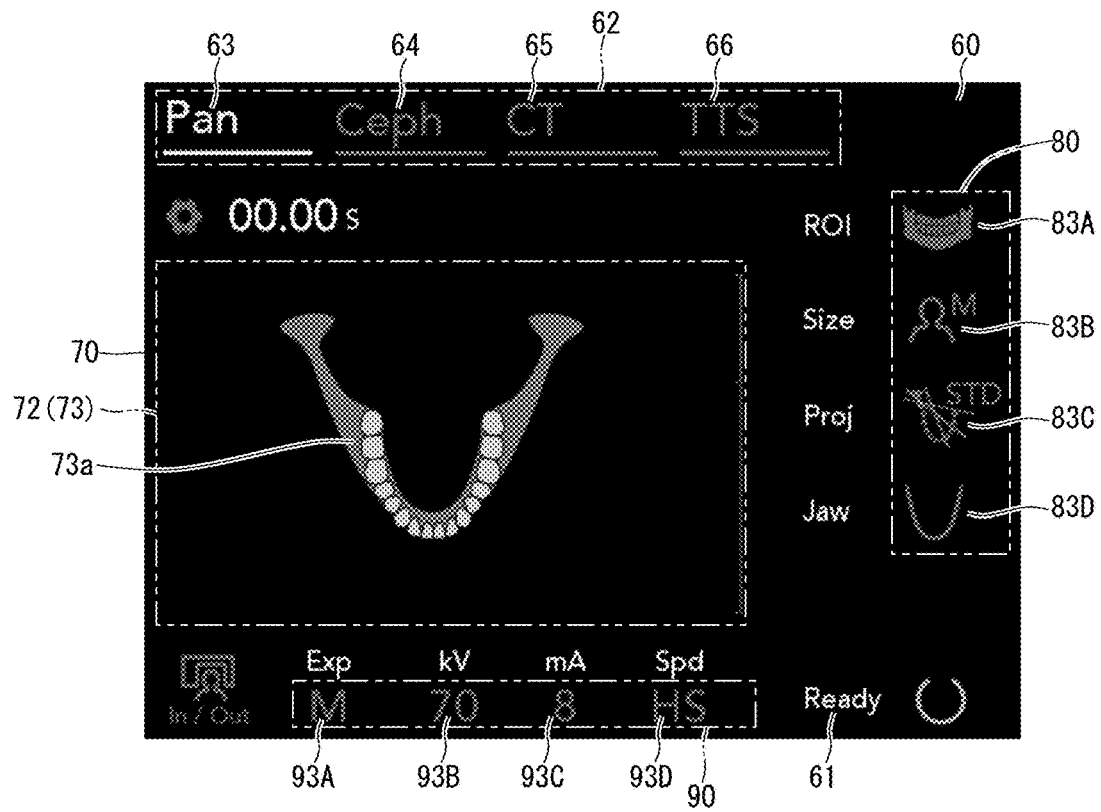
FIG. 6 is a view illustrating a display example when a panoramic photography mode selection image is selected.

As illustrated in FIG. 6, an illustration image 73a indicating a plan view of the dental arch may be displayed as the illustration image corresponding to the panoramic photography mode in the illustration display region 70.

As described above, the region-of-interest setting image 83A, the patient size selection image 83B, the projection setting image 83C, and the dental arch shape selection image 83D are displayed as the photography condition setting image corresponding to the panoramic photography mode in the first photography condition setting region 80.

As described above, the irradiation setting image 93A, the tube voltage setting image 93B, the tube current setting image 93C, and the photographing speed setting image 93D are displayed as the photography condition setting image corresponding to the panoramic photography mode in the second photography condition setting region 90.

<First Photography Condition Setting Processing>

Figure 7:
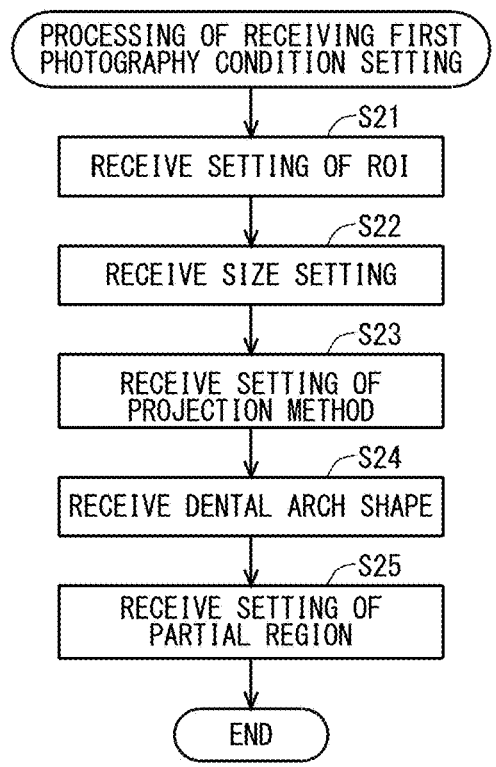
FIG. 7 is a flowchart illustrating first photography condition setting reception processing.

FIG. 7 is a flowchart illustrating the first photography condition setting reception processing in step S4.

Figure 8:
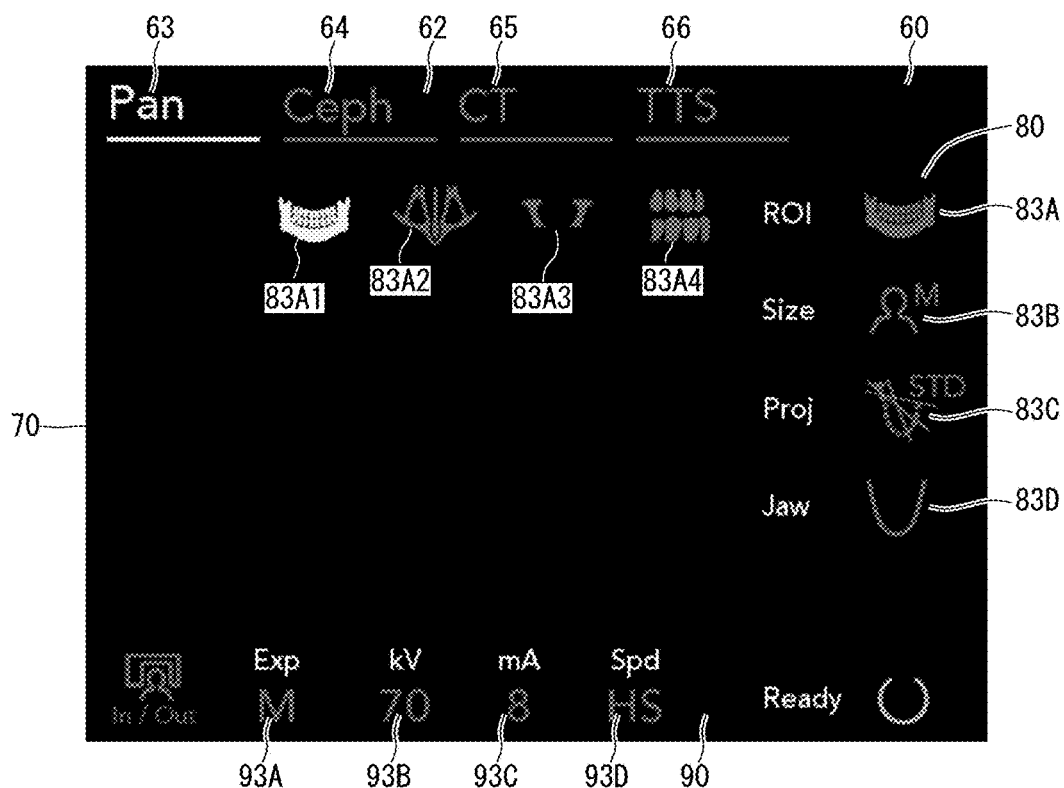
FIG. 8 is a view illustrating a display example in which plural region-of-interest setting images are displayed in a panoramic photography mode.

In step S21, the setting of the region of interest (ROI) is received using the region-of-interest setting image 83A. That is, the region-of-interest setting image 83A is the image in which the region-of-interest illustration image is added beside the characters "ROI". When the user touches the region-of-interest setting image 83A, plural region-of-interest setting images 83A1 to 83A4 are displayed as illustrated in FIG. 8. The plural region-of-interest setting images 83A1 to 83A4 include a standard panorama setting image 83A1 in which the dental arch is set to the region of interest, a maxillary sinus panorama setting image 83A2 in which the maxillary sinus is set to the region of interest, a jaw or chin joint setting image 83A3 in which a jaw or chin joint is set to the region of interest, and a right-and-left-part panorama setting image 83A4 in which right and left parts of the dental arch are set to the region of interest. When the user touches the region-of-interest setting image 83A, the images 83A1 to 83A4 are horizontally displayed instead of the illustration image 72. At this point, the currently-set region of interest is distinguishably displayed. For the example in FIG. 8, the standard panorama setting image 83A1 is displayed in color (including different shade of color) different from the other images 83A2, 83A3, and 83A4.

The setting of the region of interest (ROI) is received when the user touches one of the horizontally-displayed images 83A1 to 83A4. In the case that the reception of the setting of the region of interest is not changed, the flow goes to the next processing while the current region of interest is not changed.

In the case that the standard panorama setting image 83A1 is selected, the image in FIG. 4 is displayed subsequent to the image in FIG. 8.

Figure 9:
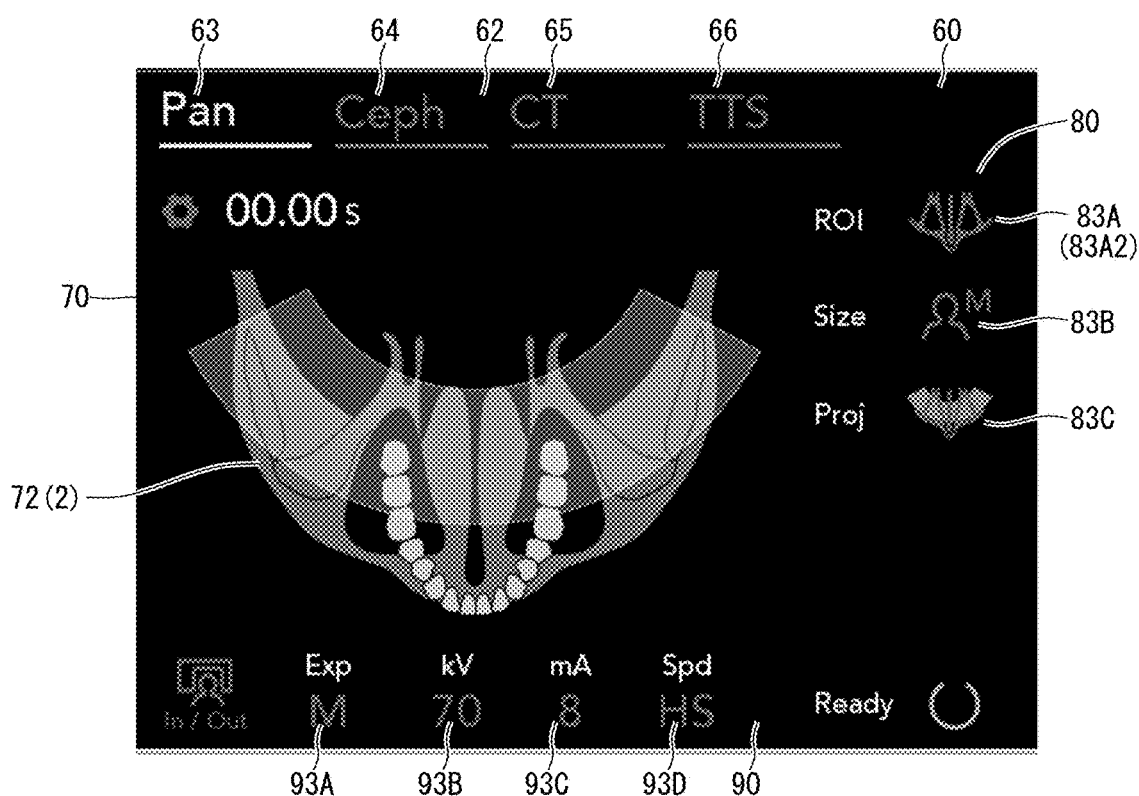
FIG. 9 is a view illustrating a display example when a maxillary sinus panorama setting image is selected in the panoramic photography mode.

In the case that the maxillary sinus panorama setting image 83A2 is selected, as illustrated in FIG. 9, the illustration image 72(2) indicating the maxillary sinus is displayed as the illustration image corresponding to the panoramic photography mode in the illustration display region 70. The region-of-interest setting image 83A2, the patient size selection image 83B, and the projection setting image 83C are displayed as the photography condition setting image corresponding to the panoramic photography mode in the first photography condition setting region 80, but the dental arch shape selection image 83D is not displayed in the first photography condition setting region 80.

FIG. 8 shows a display state of region-of-interest setting images 83A1 to 83A4. The display state shown in FIG. 9 can be accomplished, for example, by pressing the region-of-interest setting image 83A2 shown in FIG. 8.

Figure 10:
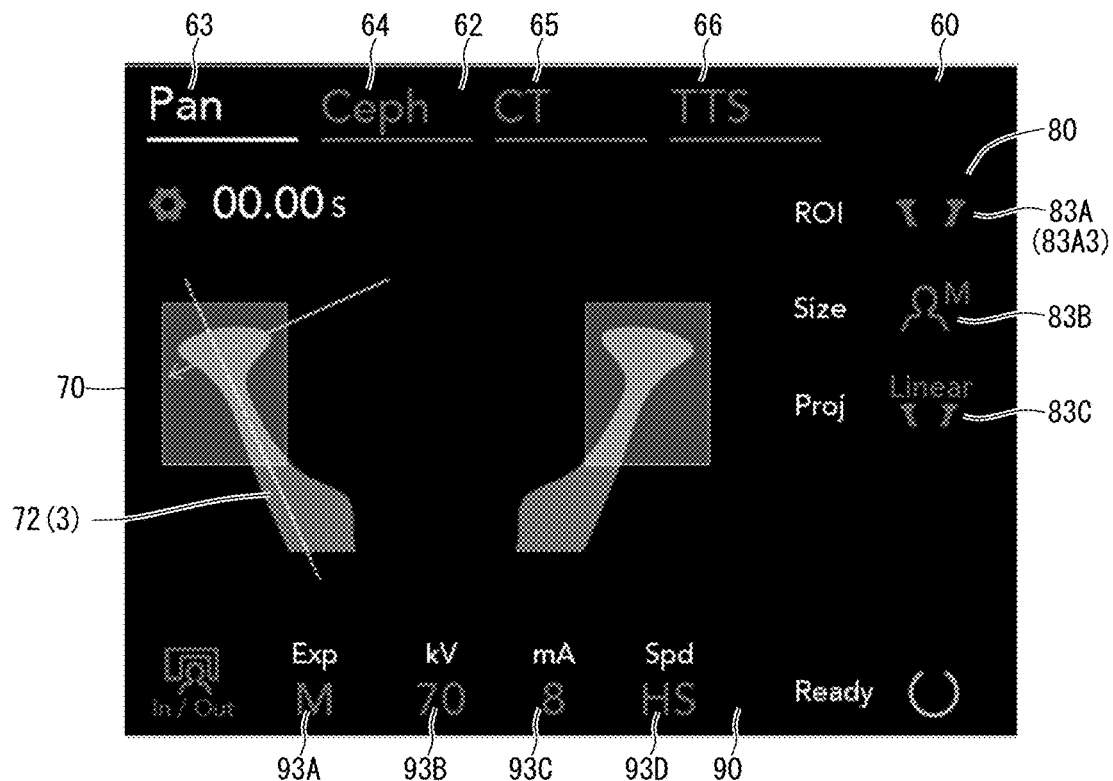
FIG. 10 is a view illustrating a display example when a jaw or chin joint setting image is selected in the panoramic photography mode.

In the case that the jaw or chin joint setting image 83A3 is selected, as illustrated in FIG. 10, the illustration image 72(3) indicating the right and left jaw or chin joints is displayed as the illustration image corresponding to the panoramic photography mode in the illustration display region 70. The region-of-interest setting image 83A3, the patient size selection image 83B, and the projection setting image 83C are displayed as the photography condition setting image corresponding to the panoramic photography mode in the first photography condition setting region 80, but the dental arch shape selection image 83D is not displayed in the first photography condition setting region 80. When the photography is started on this condition, the panoramic photography of the right and left jaw or chin joints can continuously be performed by one-time operation.

Figure 11:
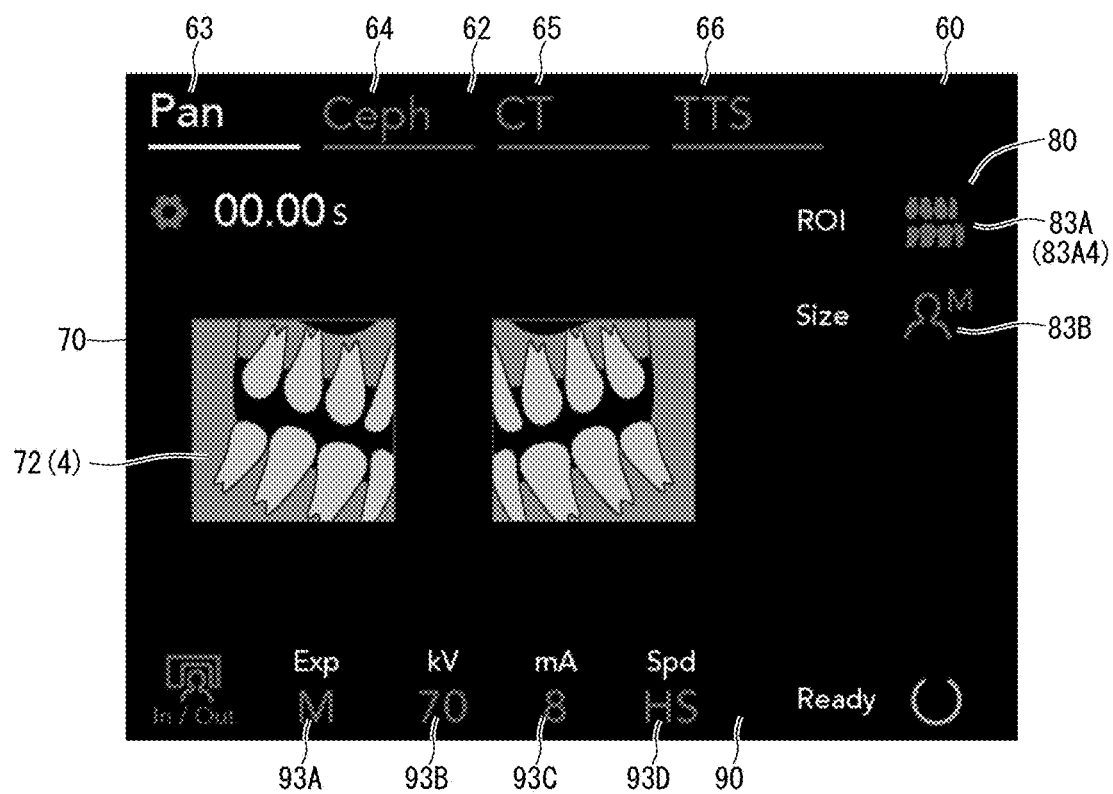
FIG. 11 is a view illustrating a display example when a right-and-left-part panorama setting image is selected in the panoramic photography mode.

In the case that the right-and-left-part panorama setting image 83A4 is selected, as illustrated in FIG. 11, the panorama illustration image 72(4) indicating the right and left parts of the dental arch is displayed as the illustration image corresponding to the panoramic photography mode in the illustration display region 70. When this condition is selected to start the photography, partial panoramic photography of the right and left tooth rows can continuously be performed by one-time operation. The region-of-interest setting image 83A and the patient size selection image 83B are displayed as the photography condition setting image corresponding to the panoramic photography mode in the first photography condition setting region 80, but the projection setting image 83C and the dental arch shape selection image 83D are not displayed in the first photography condition setting region 80.

As described above, an item that can be set as a first condition depends on the setting of the region of interest. The following processing will be described with the case that the standard panorama setting image 83A1 having the most setting items is selected as an example.

Figure 12:
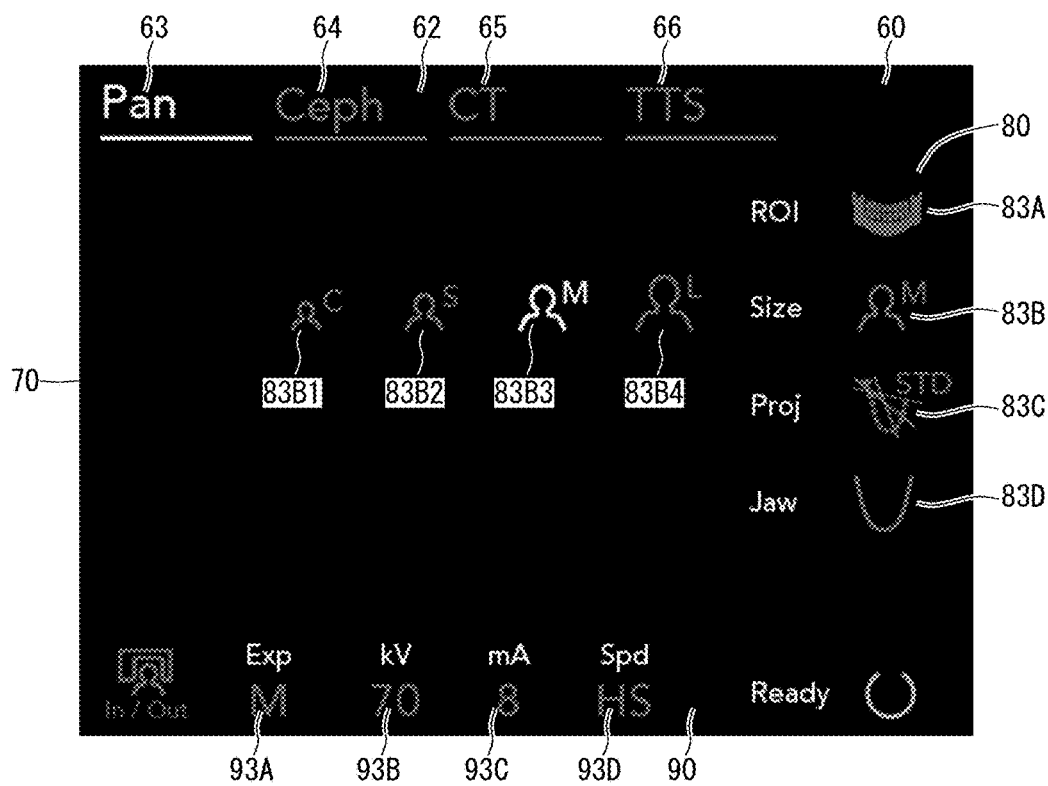
FIG. 12 is a view illustrating a display example in which plural patient size selection images are displayed.

In step S22, the setting of the size is received using the patient size selection image 83B. That is, the patient size selection image 83B is the image in which the illustration image indicating the upper half of the body and the character indicating the size are added beside the characters "Size". When the user touches the patient size selection image 83B, the plural patient size selection images 83B1 to 83B4 are displayed as illustrated in FIG. 12. The plural patient size selection images 83B1 to 83B4 include plural patient size display illustration images indicating upper body external forms having different sizes. More specifically, the plural patient size selection images 83B1 to 83B4 are images in which characters indicating the sizes are added to the plural patient size display illustration images indicating the upper body external forms. A patient size selection image 83B1 is an image in which a character "C" (the first character of a child) is added to the smallest patient size display illustration image, a patient size selection image 83B2 is an image in which a character "S" (the first character of small) is added to the second-smallest patient size display illustration image, a patient size selection image 83B3 is an image in which a character "M" (the first character of middle) is added to the third-smallest patient size display illustration image, and a patient size selection image 83B4 is an image in which a character "L" (the first character of large) is added to the largest patient size display illustration image.

When the user touches the patient size selection image 83B, the images 83B1 to 83B4 are horizontally displayed instead of the illustration image 72. At this point, the currently-set patient size is displayed while being distinguishable from other patient sizes. For the example in FIG. 12, the patient size selection image 83B3 is displayed in color (including different shade of color) different from the other images 83B1, 83B2, and 83B4.

The setting of the patient size is received when the user touches one of the horizontally-displayed images 83B1 to 83B4. In the case that the reception of the setting of the patient size is not changed, the flow goes to the next processing while the current patient size is not changed.

The processing of setting the patient size using the patient size selection image 83B is similarly performed even in the case that the photography of another region of interest is performed in the panoramic photography mode and the case that the photography is performed in another photography mode.

Figure 13:
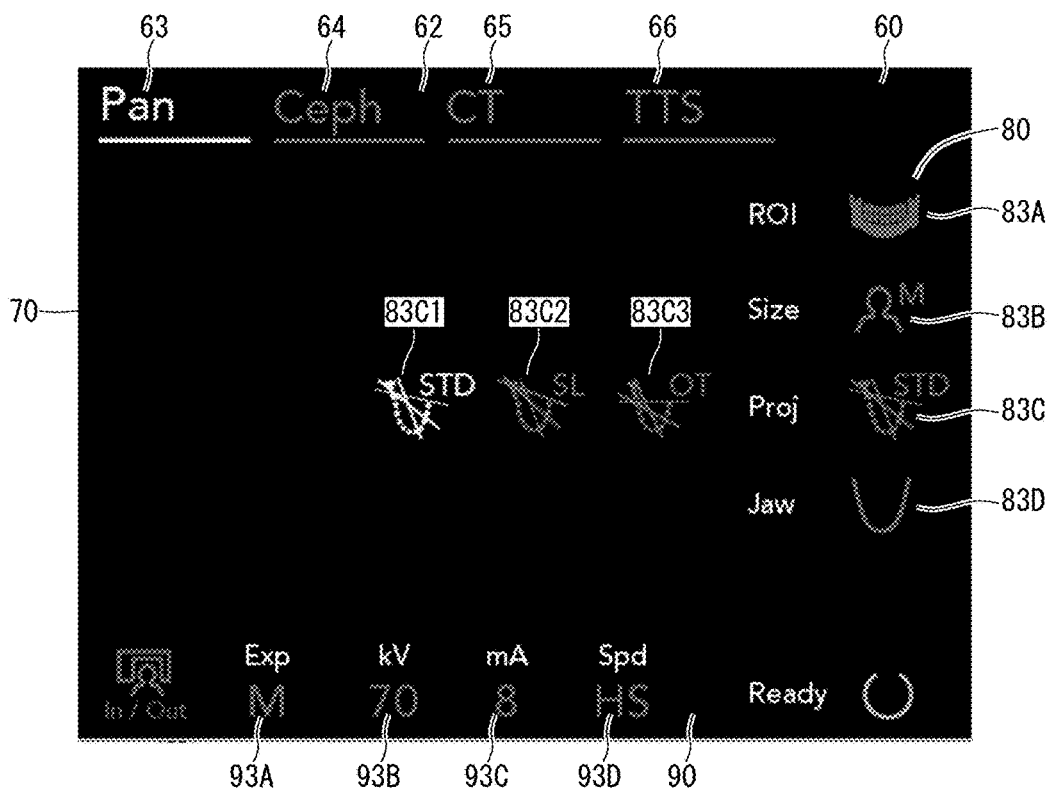
FIG. 13 is a view illustrating a display example in which plural projection setting images are displayed.

In step S23, the setting of the projection method is received using the projection setting image 83C. That is, the projection setting image 83C is the image in which the illustration image indicating the projection method and the characters indicating the projection method are added beside the characters "Proj". When the user touches the projection setting image 83C, plural projection setting images 83C1 to 83C3 are displayed as illustrated in FIG. 13. The plural projection setting images 83C1 to 83C3 indicate different projection methods. A projection setting image 83C1 indicates a projection method of performing the panoramic photography in a standard projection orbit, a projection setting image 83C2 indicates a projection method of performing the panoramic photography in a projection orbit orthogonal to a jawbone or chinbone, and a projection setting image 83C3 indicates a projection method of performing the panoramic photography in a projection orbit orthogonal to the dental arch.

When the user touches the projection setting image 83C, the images 83C1 to 83C3 are horizontally displayed instead of the illustration image 72. At this point, the currently-set projection method is displayed while being distinguishable from other projection methods. For the example in FIG. 13, the projection setting image 83C1 indicating the standard panorama is displayed in color (including different shade of color) different from the other images 83C2 and 83C3.

The setting of the projection method is received when the user touches one of the horizontally-displayed images 83C1 to 83C3. In the case that the reception of the setting of the projection method is not changed, the flow goes to the next processing while the current projection method is not changed.

Even in the panoramic photography mode, the setting of the projection method varies depending on the region of interest. The projection setting image suitable to indicate the projection method is displayed according to the set region of interest. Sometimes the projection method is not set depending on the region of interest.

Figure 14:
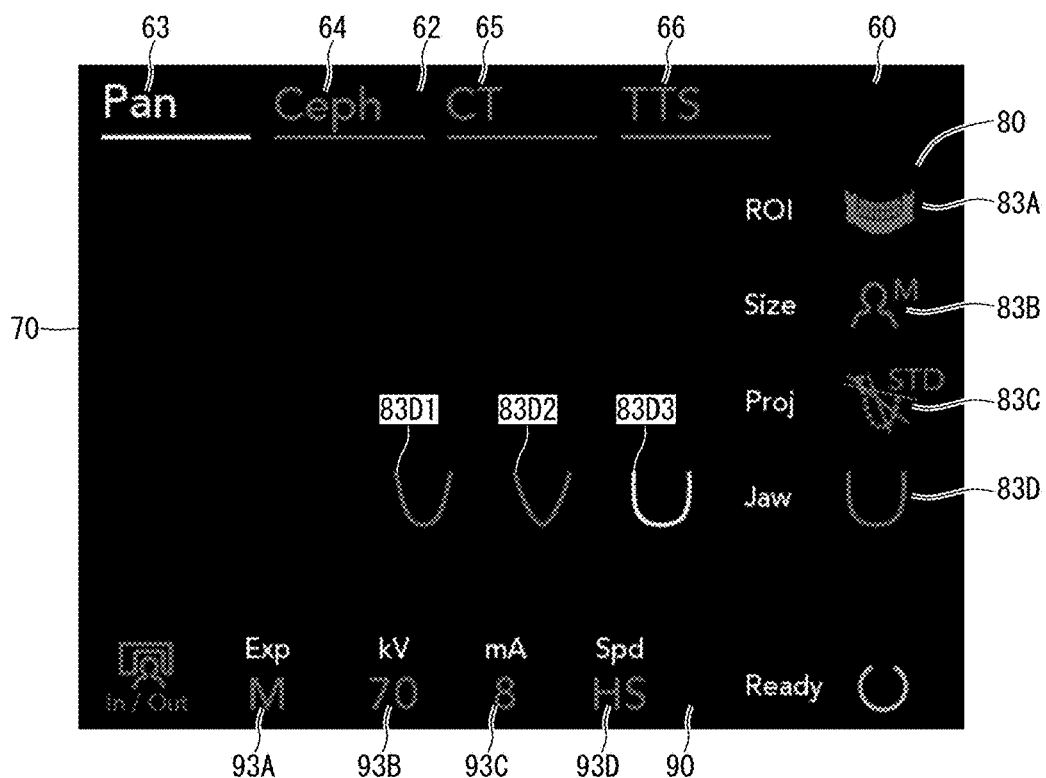
FIG. 14 is a view illustrating a display example in which plural dental arch shape selection images are displayed.

In step S24, the dental arch shape is received using the dental arch shape selection image 83D of the patient. That is, the dental arch shape selection image 83D is the image in which the illustration image indicating the dental arch is added beside the characters "Jaw" or "Chin". When the user touches the dental arch shape selection image 83D, plural dental arch shape selection images 83D1 to 83D3 are displayed as illustrated in FIG. 14. The plural dental arch shape selection images 83D1 to 83D3 indicate different shapes of dental arches. A dental arch shape selection image 83D1 includes a standard dental arch illustration image indicating a standard dental arch, a dental arch shape selection image 83D2 includes the illustration image (the dental arch illustration image having a horizontally narrow width) indicating the dental arch (the dental arch having the horizontally narrow width) in which a canine tooth projects small, and a dental arch shape selection image 83D3 includes the illustration image indicating the dental arch in which the canine tooth projects large.

When the user touches the dental arch shape selection image 83D, the images 83D1 to 83D3 are horizontally displayed instead of the illustration image 72. At this point, the currently-set projection method is displayed while being distinguishable from other projection method. For the example in FIG. 14, the dental arch shape selection image 83D3 indicating the standard dental arch is displayed in color (including different shade of color) different from the other images 83D1 and 83D2.

The setting of the dental arch shape is received when the user touches one of the horizontally-displayed images 83D1 to 83D3. In the case that the reception of the setting of the dental arch shape is not changed, the flow goes to the next processing while the current dental arch shape is not changed. In the case that the illustration image 72 indicating the plan view of the dental arch is displayed as the illustration image 72, the shape of the plan view of the dental arch displayed as the illustration image 72 may be changed according to the dental arch shape set in step S24. For example, in the case that the dental arch having the horizontally narrow width is selected, the image indicating the dental arch having the horizontally narrow width may be displayed as the illustration image 72.

Even in the panoramic photography mode, the setting screen of the dental arch shape is eliminated in the case that the photography is performed while another region of interest is set.

Figure 15:
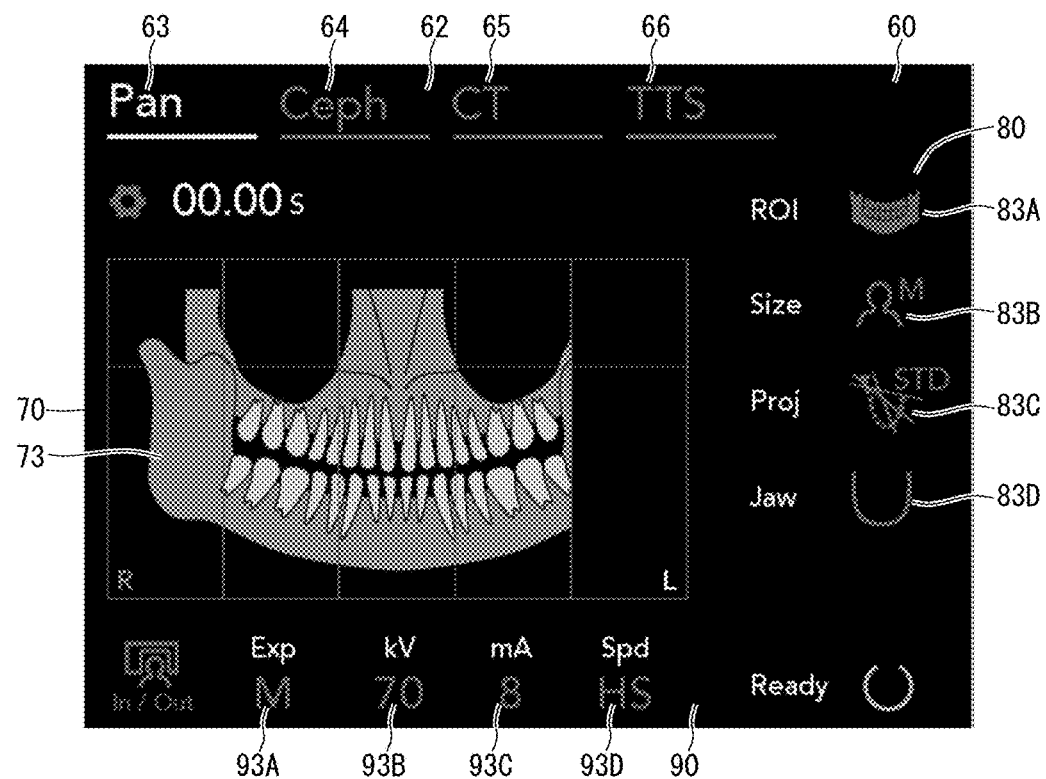
FIG. 15 is a view illustrating a display example when a photography region is selected in an illustration image.

In step S25, the setting of the partial region to be photographed is received. The setting of the partial region is received using the entire jaw or chin panorama illustration image 72 displayed in the illustration display region 70. That is, as illustrated in FIG. 4, the entire jaw or chin panorama illustration image 72 is divided into plural parts. In this case, the illustration image 72 is vertically divided into two parts, and horizontally divided into five parts. When the user touches one of the divided regions of the illustration image 72, the photography region selection operation is received as illustrated in FIG. 15. In this case, when the user touches one of the divided regions of the illustration image 72, a portion including the touched region is switched from a photography region to a non-photography region or from a non-photography region to a photography region. The switching between the photography region and the non-photography region may be performed in a unit of touched region, or a unit of plural regions including the touched region. For the latter, when the user touches one of the upper regions, it is conceivable that all the upper regions are switched between the photography region and the non-photography region.

When the photography region selection operation is received, the photography region of the selected partial panorama is displayed in the visually distinguishable manner. For the example in FIG. 15, in the entire jaw or chin panorama illustration image 72, the non-photography region is erased and the display of the photography region remains. Therefore, the photography region can be distinguished by the existence of the display.

For the example in FIGS. 4 and 15, a boundary line dividing the entire jaw or chin panorama illustration image 72 is displayed. However, the boundary line is not necessarily displayed. Examples of the configuration in which the photography region is distinguishably displayed include a configuration in which the illustration image 72 is displayed while the photography region and the non-photography region are distinguished from each other using different colors, a configuration in which the photography region is surrounded by a frame, and a configuration in which the photography region is displayed with a pattern. Therefore, an exposure dose can be reduced when the partial panorama X-ray photography is performed in the minimum region necessary for a diagnosis.

As illustrated in FIG. 6, in the case that the illustration image 73a indicating the plan view of the dental arch is displayed in the illustration display region 70, similarly the photography region selection operation may be received in a unit of plural divided regions. In this case, a curve connecting focal points is displayed along the dental arch of the illustration image 73a, and the curve is moved on the front and back of the dental arch according to the touch position, or a curvature of the curve is changed, whereby the focal point may be adjusted.

When the user touches one of the regions of the illustration image 72, the photography region selection operation is received, and the processing related to the reception of the setting of the first photography condition is ended. In the case that the reception of the setting of the photography region is not changed, the processing is ended while the current photography region is not changed.

<Second Photography Condition Setting Processing>

Figure 16:
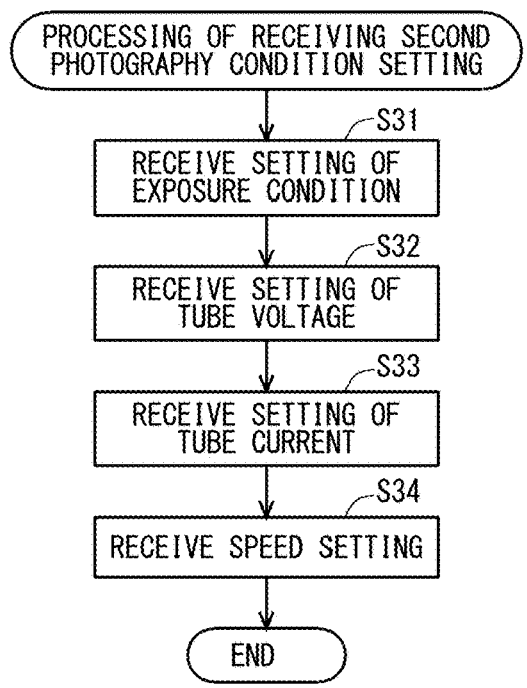
FIG. 16 is a flowchart illustrating second photography condition setting reception processing.

FIG. 16 is a flowchart illustrating the second photography condition setting reception processing in step S5.

Figure 17:
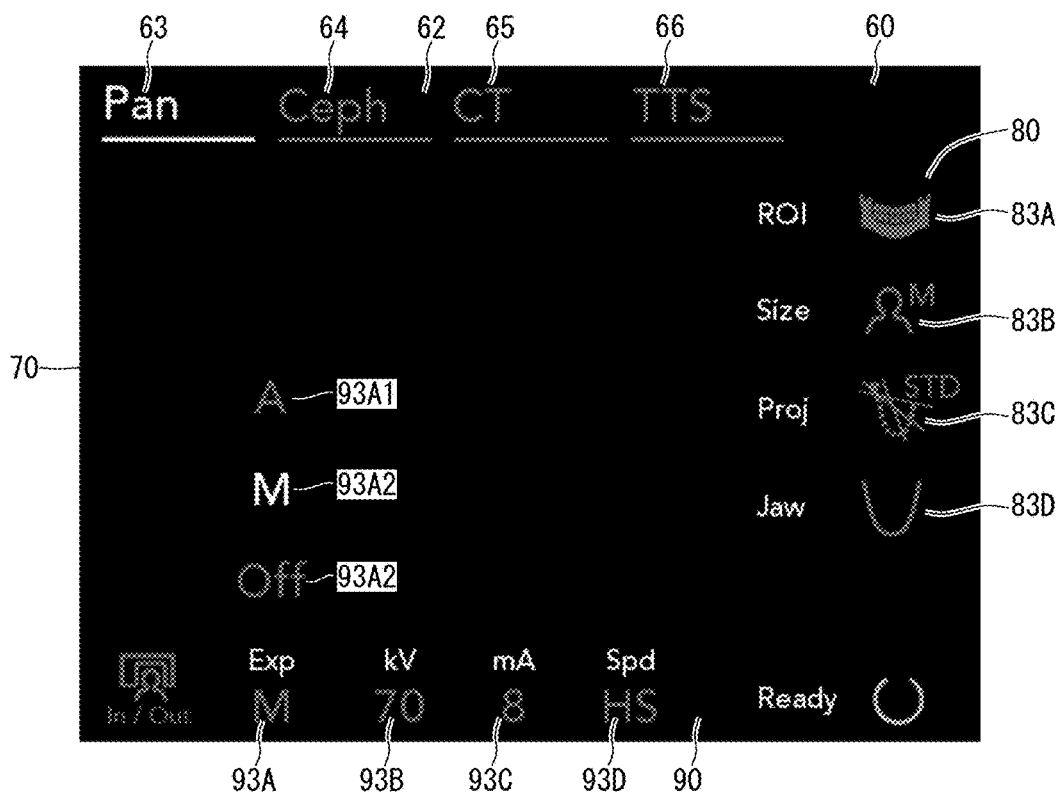
FIG. 17 is a view illustrating a display example in which plural irradiation setting images are displayed.

In step S31, the irradiation setting is performed using the irradiation setting image 93A. That is, the irradiation setting image 93A is the image in which the content of the irradiation setting is added below the characters "Exp". When the user touches the irradiation setting image 93A, irradiation setting images 93A1, 93A2, and 93A3 are displayed as illustrated in FIG. 17. An irradiation setting image 93A1 is an image, which includes a character "A" and indicates automatic setting (auto). An irradiation setting image 93A2 is an image, which includes a character "M" and indicates manual setting (manual). An irradiation setting image 93A3 is an image, which includes characters "Off" and indicates turn-off of the X-ray (it is set in the case that the arm is turned without the irradiation).

When the user touches the irradiation setting image 93A, the images 93A1, 93A2, and 93A3 are vertically displayed instead of the illustration image 72. At this point, the currently-set irradiation setting (in this case, "M" setting) is distinguishably displayed.

When the user touches one of the images 93A1, 93A2, and 93A3, the irradiation setting is received. In the case that the reception of the irradiation setting is not changed, the current irradiation setting is applied as is.

Figure 18:
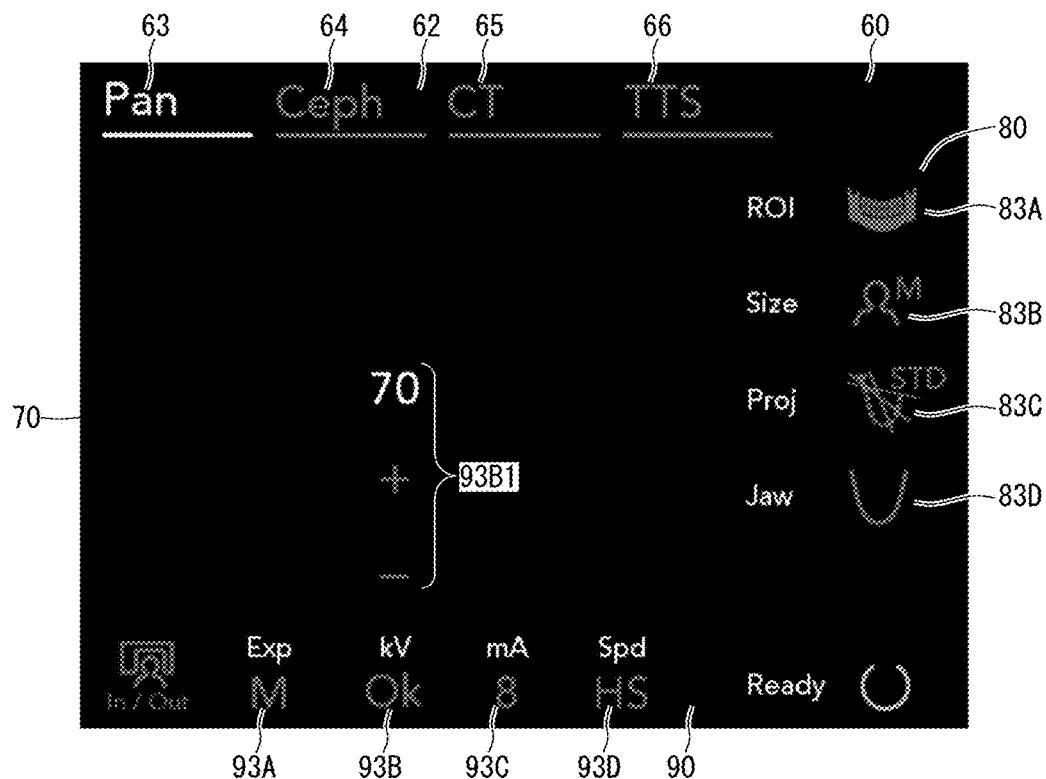
FIG. 18 is a view illustrating a display example of a tube voltage adjustment image.

In step S32, the tube voltage is set using the tube voltage setting image 93B. That is, the tube voltage setting image 93B is the image in which a numerical value of the tube voltage is displayed below the unit of voltage "kV". When the user touches the tube voltage setting image 93B, a tube voltage adjustment image 93B1 is displayed instead of the illustration image 72 as illustrated in FIG. 18. The tube voltage adjustment image 93B1 includes a symbol "+" increasing the tube voltage, a symbol "−" decreasing the tube voltage, and a numerical value display place indicating the tube voltage. The tube voltage setting value increases when the user touches the symbol "+", the tube voltage setting value decreases when the user touches the symbol "−", and each setting value is displayed as the numerical value. While the tube voltage adjustment image 93B1 is displayed, the image indicating characters "OK" is displayed instead of the numerical value in the numerical value display place of the tube voltage setting image 93B. When the user touches the image indicating the characters "OK" after the setting of the tube voltage, the tube voltage adjustment image 93B1 is eliminated, the illustration image 72 is displayed again, and the tube voltage setting image 93B is displayed while the setting value is reflected.

Figure 19:
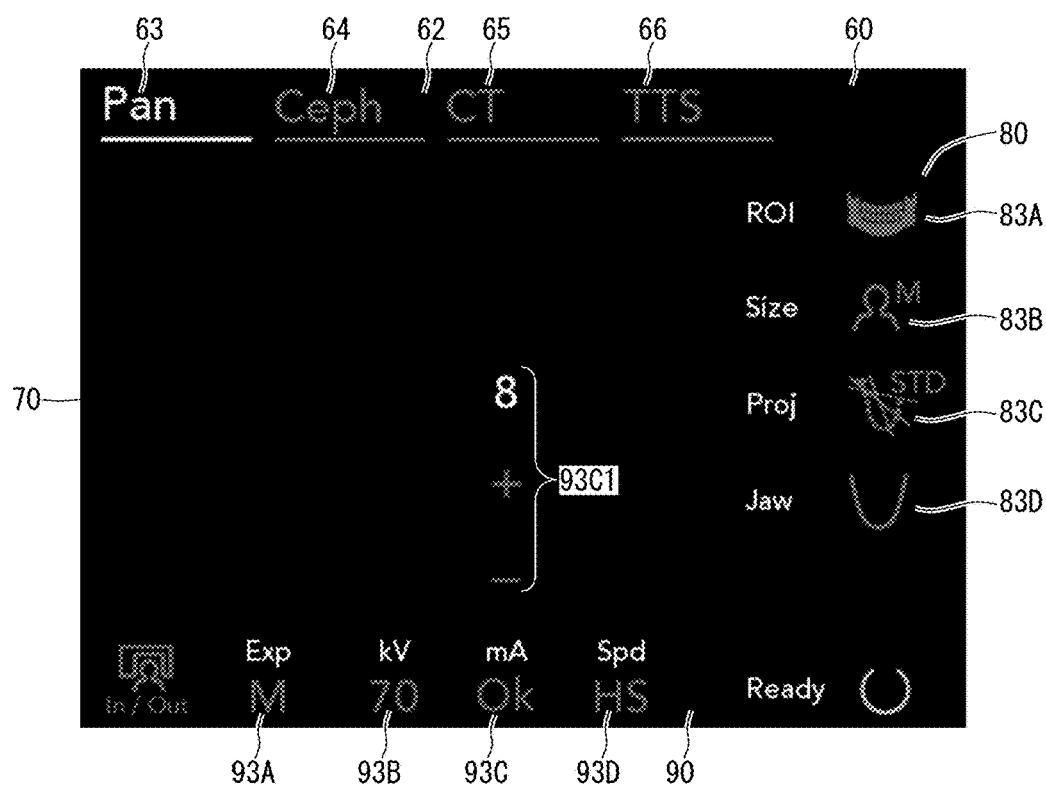
FIG. 19 is a view illustrating a display example of a tube current adjustment image.

In step S33, the tube current is set using the tube current setting image 93C. That is, the tube current setting image 93C is the image in which a numerical value of the tube current is displayed below the unit of current "mA". When the user touches the tube current setting image 93C, the tube current adjustment image 93C1 is displayed instead of the illustration image 72 as illustrated in FIG. 19. The tube voltage adjustment image 93C1 includes a symbol "+" increasing the tube current, a symbol "−" decreasing the tube current, and a numerical value display place indicating the tube current. The tube current setting value increases when the user touches the symbol "+", the tube current setting value decreases when the user touches the symbol "−", and each setting value is displayed as the numerical value. While the tube current adjustment image 93C1 is displayed, the image indicating the characters "OK" is displayed instead of the numerical value in the numerical value display place of the tube current setting image 93C. When the user touches the image indicating the characters "OK" after the setting of the tube current, the tube current adjustment image 93C1 is eliminated, the illustration image 72 is displayed again, and the tube current setting image 93C is displayed while the setting value is reflected.

Figure 20:
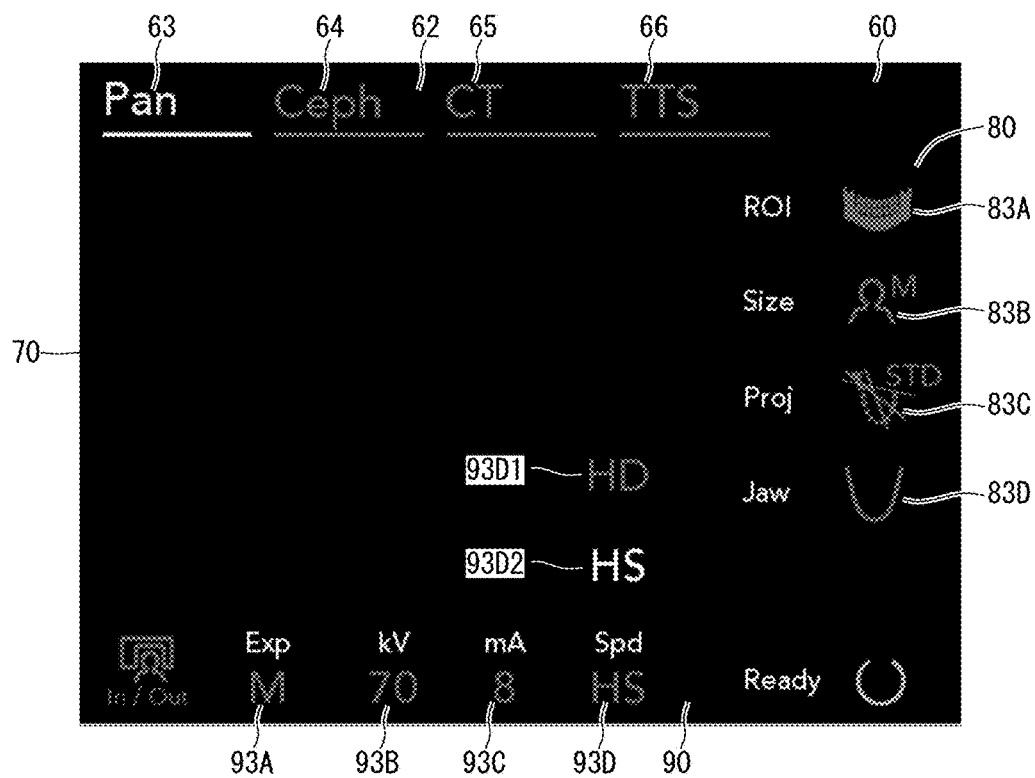
FIG. 20 is a view illustrating a display example of plural photographing speed setting images.

In step S34, the photographing speed setting is received using the photographing speed setting image 93D. That is, the photographing speed setting image 93D is the image in which a speed setting state is added below the characters "Spd". When the user touches the photographing speed setting image 93D, plural photographing speed setting images 93D1 and 93D2 are displayed instead of the illustration image 72 as illustrated in FIG. 20. The photographing speed setting image 93D1 is the image, which includes characters "HD" and indicates standard speed. The photographing speed setting image 93D2 includes characters "HS" and indicates high speed. When the user touches one of the photographing speed setting images 93D1 and 93D2, the photographing speed is set to the standard speed or the high speed. The display of the photographing speed setting images 93D1 and 93D2 is eliminated according to the setting of the photographing speed, the illustration image 72 is displayed again, and the photographing speed setting image 93D is displayed while the setting is reflected.

In the case that the automatic setting or the off setting is performed in step 31, the tube voltage setting image 93B and the tube current setting image 93C can be eliminated, or changed to another setting image.

It is possible that the embodiment example of the first and second photography condition setting processing can be regarded as an embodiment example of a processing to display a plurality of photography condition setting images corresponding to a plurality of photography conditions in or on a photography condition setting region.

The photography conditions may contain a photography condition comprising a plurality of subordinate photography conditions into which the photography condition is divided (The photography condition is a superordinate photography condition against the subordinate photography conditions).

For example, the first photography conditions may contain a photography condition such as a region-of-interest setting (83A in FIG. 8) as well as a plurality of photography conditions as subordinate photography conditions (83A1 to 83A4 in FIG. 8).

The subordinate photography conditions may contain a photography condition (83A2 in FIG. 8) comprising a plurality of next subordinate photography conditions (83B, 83C in FIG. 9) into which the subordinate photography condition is divided (The subordinate photography condition is a superordinate photography condition against the next subordinate photography conditions).

For example, the region of interest setting (83A in FIG. 8) may comprise a plurality of photography conditions such as a standard panorama setting, a maxillary sinus panorama setting, a jaw or chin joint setting, and/or a right-and-left-part panorama setting as subordinate photography conditions (83A1 to 83A4 in FIG. 8).

The maxillary sinus panorama setting (83A2 in FIG. 8) may comprise a plurality of photography conditions such as a patient size selection and/or projection setting (83B, 83C in FIG. 9) as next subordinate photography conditions.

A setting of the subordinate photography condition may be reflected on a display of a photography condition setting image of superordinate photography condition. For example, as shown in FIG. 20, the selection of photographing speed setting images 93D1 and 93D2 is reflected on the photographing speed setting image 93D (By the selection of photographing speed setting image 93D2, "HS" is displayed in the photographing speed setting image 93D).

As described in the explanation about FIG. 20, it is possible to replace a display of an image for another one between a timing of setting and other timing.

For example, the display of the illustration image 72 is replaced for the display of the photography condition setting images 93D1, 93D2 when the timing of the photography condition setting, and after the setting, the display of the photography condition setting images 93D1, 93D2 is replaced for the display of the illustration image 72.

It is possible to replace a display of an image for another one between timing of superordinate photography condition setting and timing of subordinate photography condition setting.

The above may be preferable for a display area of a display panel with a limited width.

<Display Processing in Cephalo Photography Mode>

Figure 21:
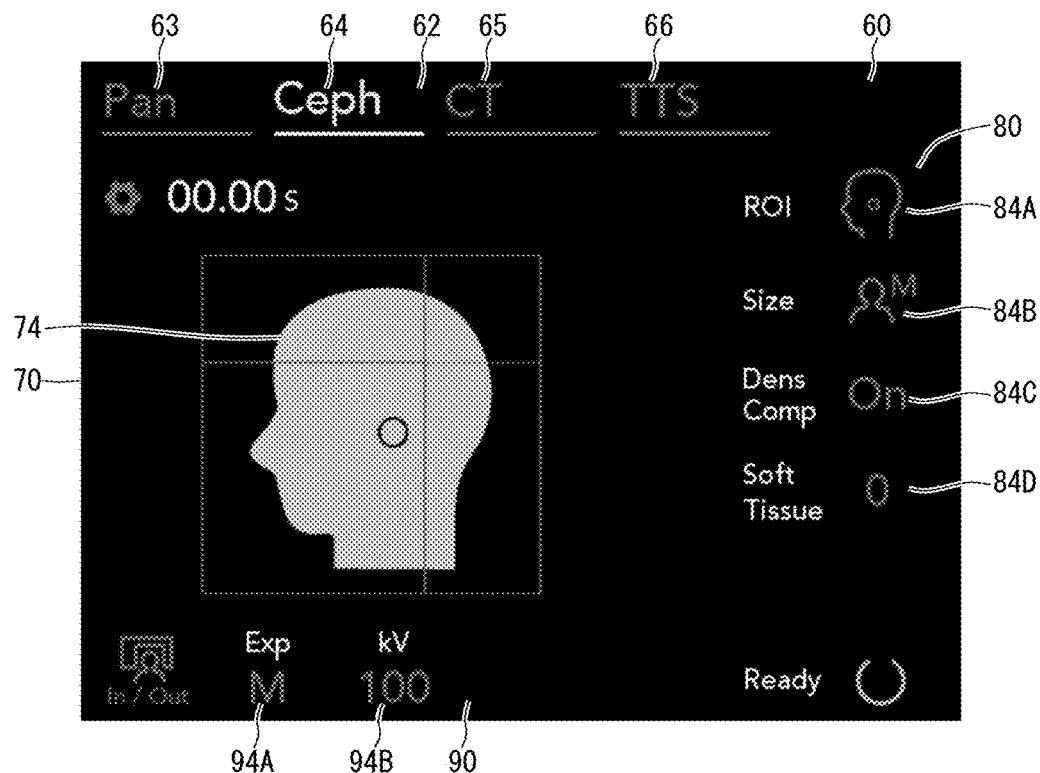
FIG. 21 is a view illustrating a display example when a cephalo photography mode is selected.

FIG. 21 is a view illustrating a display image example of a display unit 38a when the cephalo photography mode is selected. Referring to FIG. 21, the display image example on the display unit 38a includes the photography mode selection region 62, the illustration display region 70, the first photography condition setting region 80, and the second photography condition setting region 90.

The case that the cephalo photography mode selection image 64 is displayed in color (including different shade of color) different from the mode selection images 63, 65, and 66 while being distinguishable from the mode selection images 63, 65, and 66 is illustrated in the photography mode selection region 62.

For the example in FIG. 21, an illustration image 74 indicating a side face of the external head shape is displayed as the illustration image corresponding to the cephalo photography mode in the illustration display region 70. As described later, sometimes an illustration image indicating the front of the external head shape or an illustration image indicating the oblique rear of the external head shape is displayed as the illustration image corresponding to the cephalo photography mode. In the preferred embodiment, a hand can be photographed when the cephalo photography mode is selected. Therefore, sometimes the illustration image of the hand is displayed in the case that the cephalo photography mode is selected and that the hand is set to the region of interest.

A region-of-interest setting image 84A, a patient size selection image 84B, a density correction setting image 84C, and a density correction start position setting image 84D are displayed as the photography condition setting image corresponding to the cephalo photography mode in the first photography condition setting region 80. According to the setting content of the region-of-interest setting image 84A, the existence of the display of one of the images 84B, 84C, and 84D can be changed, or the images 84B, 84C, and 84D can be changed to another image.

An irradiation setting image 94A and a tube voltage setting image 94B are displayed as the photography condition setting image corresponding to the cephalo photography mode in the second photography condition setting region 90. According to the setting content of the region-of-interest setting image 84A, another image (for example, the tube current setting image) can be added to the second photography condition setting region 90.

The setting of the region of interest, the selection of the patient size, the setting of existence of density correction, and the setting of the density correction start position are received using the first photography condition setting region 80. The reception setting processing in each of the region-of-interest setting image 84A and patient size selection image 84B is similar to that in the panoramic photography mode. In the processing of receiving each setting using the density correction setting image 84C, a soft tissue and a hard tissue can simultaneously be drawn by putting the display of the density correction setting image 84C into an on state, and the soft tissue is not drawn by putting the display into an off state. In the processing of receiving each setting using the density correction start position setting image 84D, when the display of the density correction start position setting image 84D is put into the on state, a numerical character indicating a density correction start position is displayed stepwise on a head illustration displayed in the illustration image display region 72, and the density correction start position and a density correction direction can be set back and forth in a stepwise manner from a surface of the soft tissue of the subject.

Figure 22:
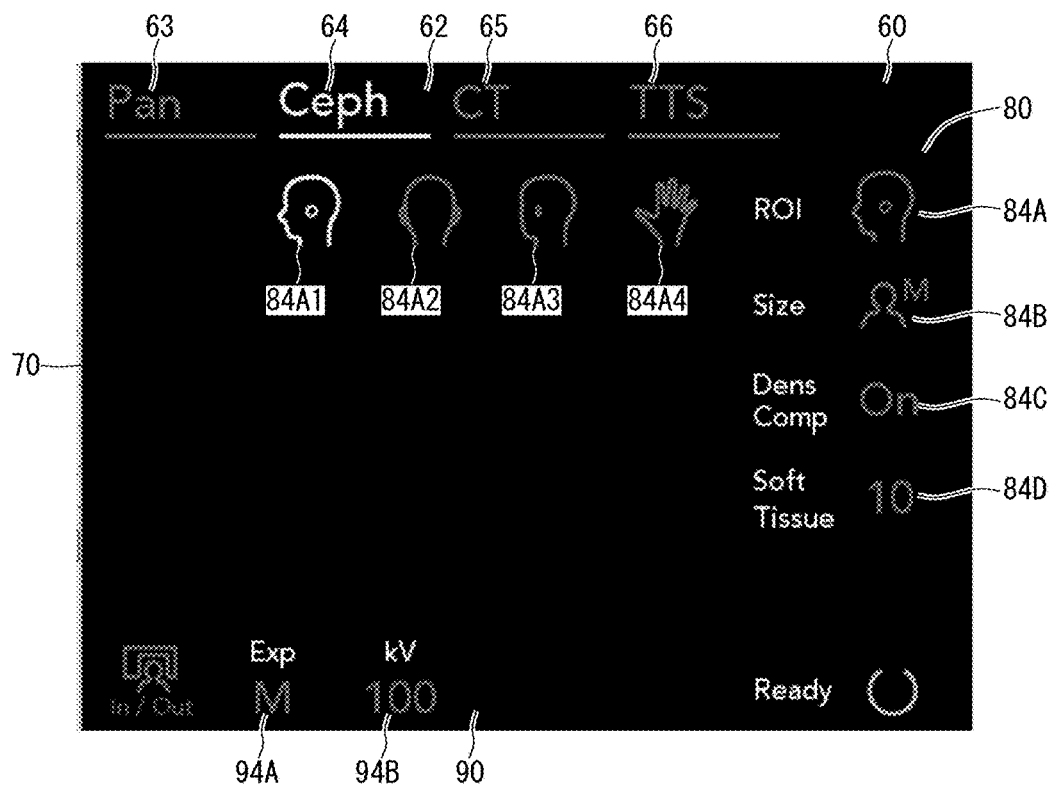
FIG. 22 is a view illustrating a display example in which plural region-of-interest setting images are displayed in the cephalo photography mode.

There is display processing in the case that the region-of-interest setting image 84A is selectively received as a recognizable processing example that is one of features in the cephalo photography mode. That is, the region-of-interest setting image 84A is the image in which the region-of-interest illustration image is added beside the characters "ROI". The region-of-interest setting image 84A can also be recognized as the photography region selection image. When the user touches the region-of-interest setting image 84A, plural region-of-interest setting images 84A1 to 84A4 are displayed as illustrated in FIG. 22. The plural region-of-interest setting images 84A1 to 84A4 indicate different regions of interest (photography regions). A region-of-interest setting image 84A1 includes the illustration image indicating the head side external form, a region-of-interest setting image 84A2 includes the illustration image indicating the head front external form, a region-of-interest setting image 84A3 includes the illustration image indicating the head obliquely-rear external form, and a region-of-interest setting image 84A4 includes the illustration image indicating the hand external form.

The region-of-interest setting image 84A1 may be prepared for front cephalo photography. The region-of-interest setting image 84A2 may be prepared for side cephalo photography. The region-of-interest setting image 84A3 may be prepared for X-ray projection image photography in an angle between the front cephalo photography and the side cephalo photography. The region-of-interest setting image 84A4 may be prepared for X-ray projection image photography of a hand.

When the user touches the region-of-interest setting image 84A, the images 84A1 to 84A4 are horizontally displayed instead of the illustration image 72. At this point, the currently-set region of interest is distinguishably displayed. When the user touches one of the horizontally-displayed images 84A1 to 84A4, the setting of the region of interest (ROI) is received. In the case that the reception of the setting of the region of interest is not changed, the flow goes to the next processing while the current region of interest is not changed.

The reception of the selected setting of the region of interest also reflects the illustration image 72. That is, the illustration image indicating the head front external form is displayed similarly to the region-of-interest setting image 84A2 when the region-of-interest setting image 84A2 is selectively received, the illustration image indicating the head obliquely-rear external form is displayed similarly to the region-of-interest setting image 84A3 when the region-of-interest setting image 84A3 is selectively received, and, when the region-of-interest setting image 84A4 is selectively received, the illustration image indicating the hand external form is displayed similarly to the region-of-interest setting image 84A4 and an X-ray transmission image of the hand can be taken by putting a palm on the photography position.

Thus, the setting of the region of interest is received, and the setting reception processing is performed on other first photography conditions.

Figure 23:
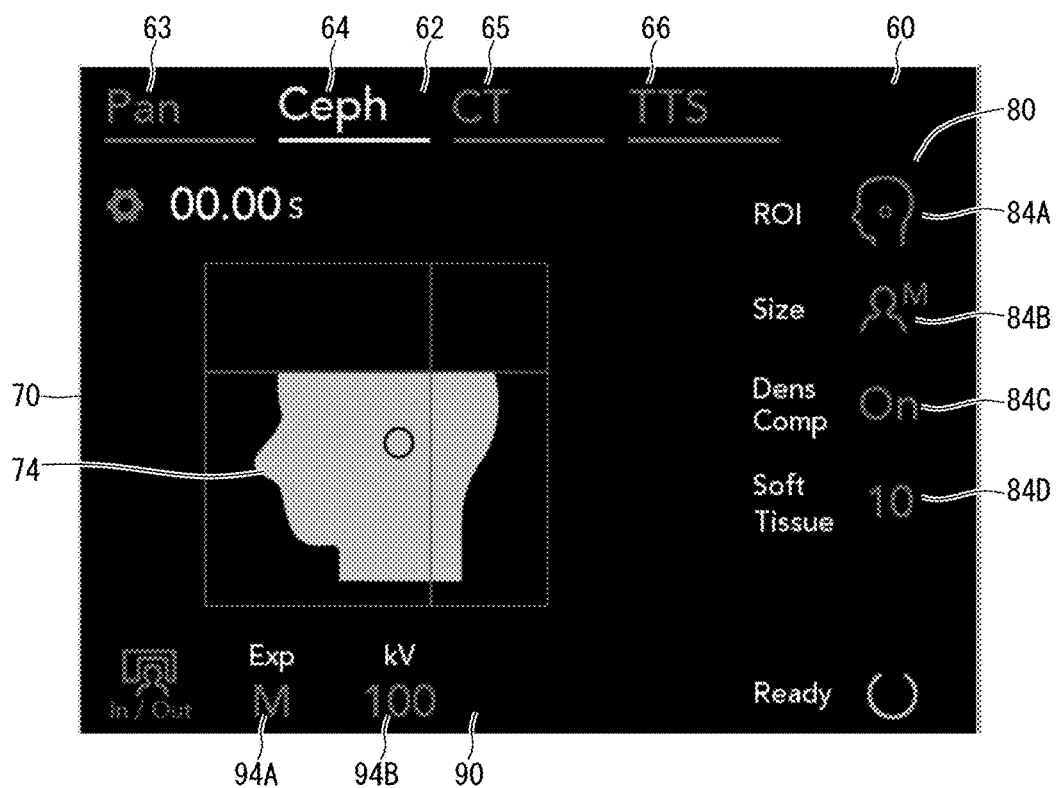
FIG. 23 is a view illustrating a display example when the photography region is selected in the illustration image.

In the cephalo photography mode, the setting of the partial region to be photographed can be received using the illustration image 74. For example, the setting of the partial region is received using the illustration image 74 indicating the side face of the external head shape displayed in the illustration display region 70. That is, as illustrated in FIG. 21, the illustration image 74 indicating the side face of the external head shape is divided into plural regions. In this case the illustration image 74 is vertically divided into two regions, and horizontally divided into two regions. When the user touches one of the divided regions of the illustration image 74, the photography region selection operation is received as illustrated in FIG. 23. When the user touches one of the divided regions of the illustration image 74, the portion including the touched region is switched from the photography region to the non-photography region or from the non-photography region to the photography region. The switching between the photography region and the non-photography region may be performed in a unit of touched region or a unit of plural regions including the touched region. For the latter, when the user touches one of the upper regions, it is conceivable that all the upper regions are switched between the photography region and the non-photography region.

When the photography region selection operation is received, the photography region of the selected partial panorama is displayed in the visually distinguishable manner. For the example in FIG. 23, in the illustration image 74 indicating the side face of the external head shape, the portion (upper portion) in the non-photography region is erased and the display of the portion (lower portion) in the photography region remains. Therefore, the photography region can be distinguished by the existence of the display.

The boundary line dividing the illustration image 74 is not necessarily displayed. Examples of the configuration in which the photography region is distinguishably displayed include a configuration in which the illustration image 74 is displayed while the photography region and the non-photography region are distinguished from each other using different colors, a configuration in which the photography region is surrounded by a frame, and a configuration in which the photography region is displayed with a pattern.

Figure 24:
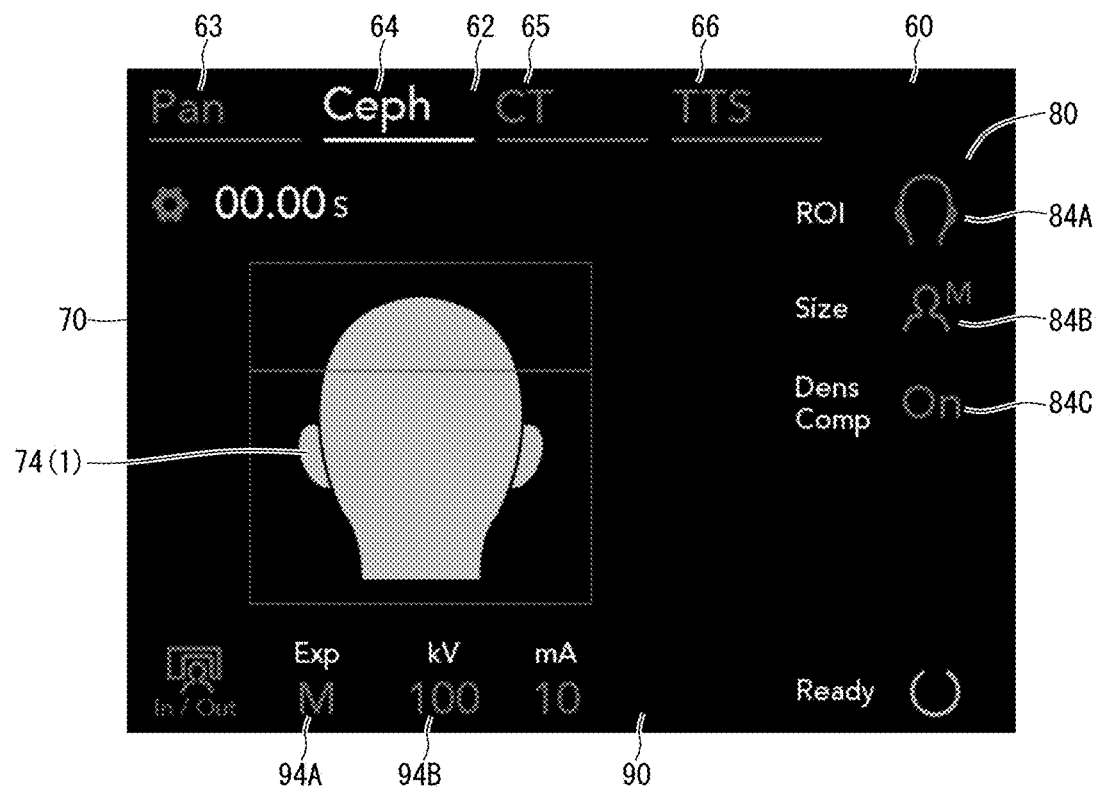
FIG. 24 is a view illustrating another display example when the cephalo photography mode is selected.

As illustrated in FIG. 24, in the case that the illustration image 74(1) indicating the front of the external head shape is displayed in the illustration display region 70, similarly the photography region selection operation may be received in a unit of plural divided regions. Although the boundary line dividing the cephalo photography illustration image 74 is displayed in the examples of FIGS. 21, 23, and 24, the boundary line is not necessarily displayed. Examples of the configuration in which the photography region is distinguishably displayed include a configuration in which the illustration image 74 is displayed while the photography region and the non-photography region are distinguished from each other using different colors, a configuration in which the photography region is surrounded by a frame, and a configuration in which the photography region is displayed with a pattern. Therefore, the exposure dose can be reduced when the partial cephalo X-ray photography is performed in the minimum region necessary for the diagnosis.

When the user touches one of the regions of the illustration image 74, the photography region selection operation is received, and the processing related to the reception of the setting of the first photography condition is ended. In the case that the reception of the setting of the photography region is not changed, the processing is ended while the current photography region is not changed.

The description of the second photography condition setting processing will be omitted because the second photography condition setting processing is similar to the setting reception processing in the panoramic photography mode.

<Display Processing in CT Photography Mode>

Figure 25:
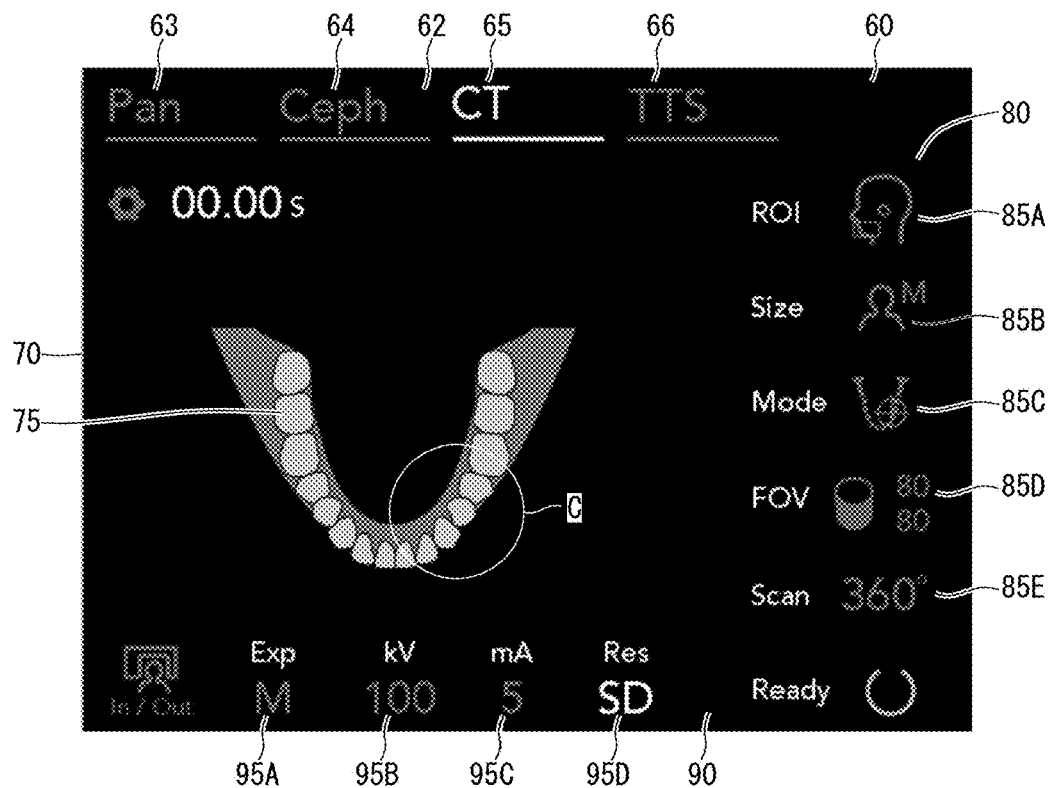
FIG. 25 is a view illustrating a display example when a CT photography mode is selected.

FIG. 25 is a view illustrating a display image example of the display unit 38a when the CT photography mode is selected. Referring to FIG. 25, the display image example on the display unit 38a includes the photography mode selection region 62, the illustration display region 70, the first photography condition setting region 80, the second photography condition setting region 90.

The case that the CT photography mode selection image 65 is displayed in color (including different shade of color) different from the mode selection images 63, 64, and 66 while being distinguishable from the mode selection images 63, 64, and 66 is illustrated in the photography mode selection region 62.

For the example in FIG. 25, an illustration image 75 indicating the plan view of the dental arch is displayed as the illustration image corresponding to the CT photography mode in the illustration display region 70. Sometimes an illustration image indicating the plan view of the dental arch including the jaw or chin joint or an illustration image indicating the plan view of the jaw or chin joint is displayed as the illustration image corresponding to the CT photography mode.

A region-of-interest setting image 85A, a patient size selection image 85B, a CT photography mode selection image 85C, a photography region setting image 85D, and a scan mode selection image 85E are displayed as the photography condition setting image corresponding to the CT photography mode in the first photography condition setting region 80. According to the setting content of the region-of-interest setting image 85A, the existence of the display of one of the images 85B, 85C, 85D, and 85E can be changed, or the images 85B, 85C, 85D, and 85E can be changed to another image.

An irradiation setting image 95A, a tube voltage setting image 95B, a tube current setting image 95C, and a resolution setting image 95D are displayed as the photography condition setting image corresponding to the CT photography mode in the second photography condition setting region 90.

The setting of the region of interest, the selection of the patient size, the selection of the CT photography mode, the setting of the photography region, the selection of a scan mode and the like are received using the first photography condition setting region 80. The reception setting processing using each of the irradiation setting image 95A, the tube voltage setting image 95B, the tube current setting image 95C, and the resolution setting image 95 is similar to that in the panoramic photography mode except for a specific content of each setting and the kind of each image.

Figure 26:
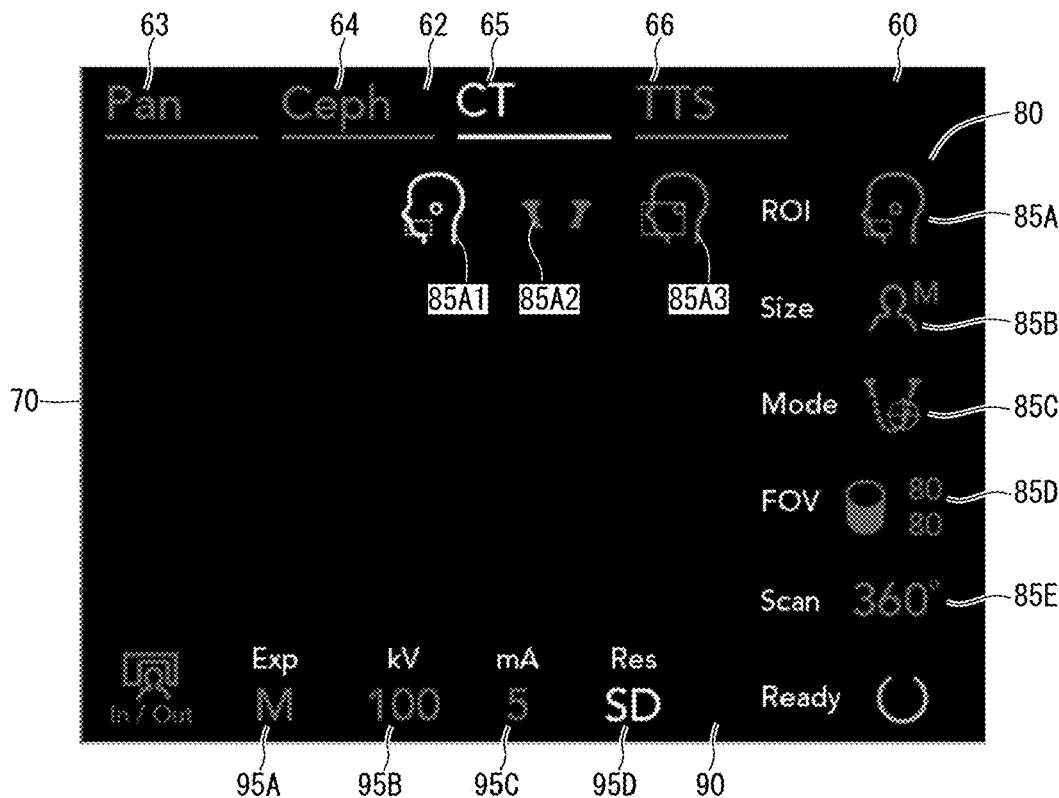
FIG. 26 is a view illustrating a display example when plural region-of-interest setting images are displayed in the CT photography mode.

There is display processing in the case that the region-of-interest setting image 85A is selectively received as a recognizable processing example that is one of features in the CT photography mode. That is, the region-of-interest setting image 85A is the image in which the region-of-interest illustration image is added beside the characters "ROI". When the user touches the region-of-interest setting image 85A, plural region-of-interest setting images 85A1 to 85A3 are displayed as illustrated in FIG. 26. The plural region-of-interest setting images 85A1 to 85A3 indicate different regions of interest (photography regions). A region-of-interest setting image 85A1 includes the illustration image indicating the side face of the whole dental arch, a region-of-interest setting image 85A2 includes the illustration image indicating the jaw or chin joint in planar view, and a region-of-interest setting image 85A3 includes the illustration image indicating the side view of the whole dental arch including the jaw or chin joint. When the user touches the region-of-interest setting image 85A, the images 85A1 to 85A3 are horizontally displayed instead of the illustration image 72. At this point, the currently-set region of interest is distinguishably displayed. When the user touches one of the horizontally-displayed images 85A1 to 85A3, the setting of the region of interest (ROI) is received. In the case that the reception of the setting of the region of interest is not changed, the flow goes to the next processing while the current region of interest is not changed.

Figure 27:
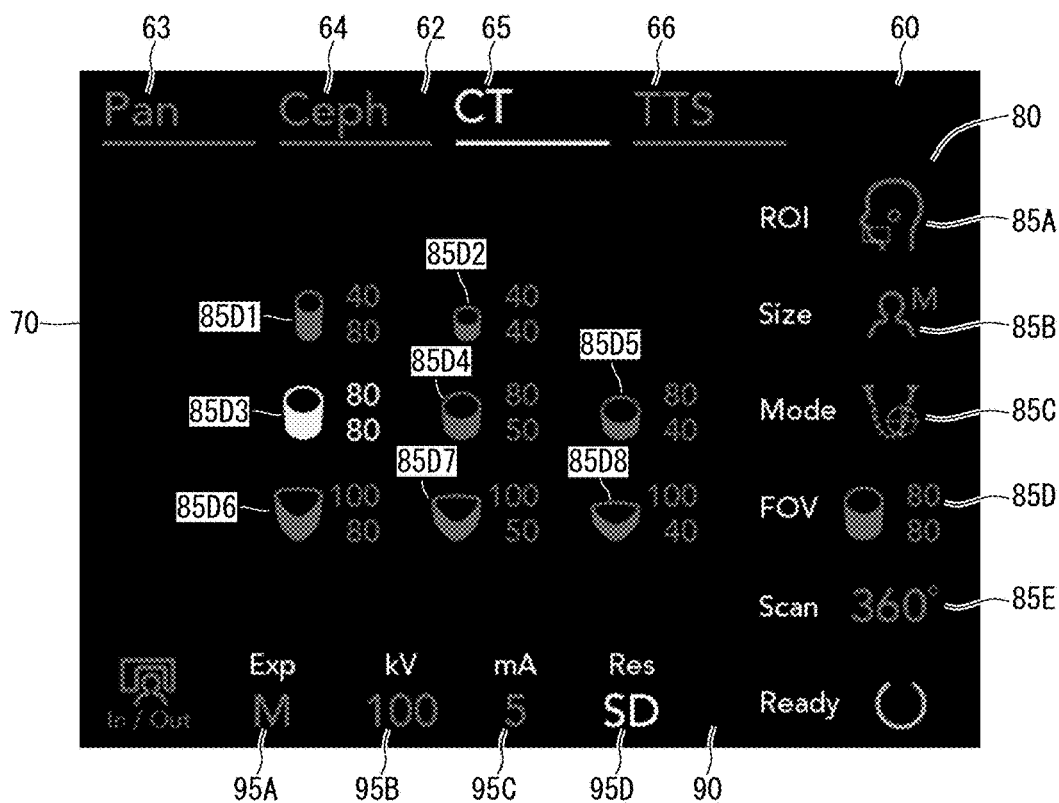
FIG. 27 is a view illustrating a display example of plural photography region setting images.

The reception of the selected setting of the region of interest also reflects the illustration image 72. That is, the illustration image indicating the jaw or chin joint in planar view is displayed similarly to the region-of-interest setting image 85A2 when the region-of-interest setting image 85A2 is selectively received, the illustration image indicating the side view of the whole dental arch including the jaw or chin joint is displayed similarly to the region-of-interest setting image 85A3 when the region-of-interest setting image 85A3 is selectively received, and the display of the FOV 85D in FIG. 27 is enlarged to the large photography region having values 150 and 150, and the photography region is photographed.

In the case that the setting of the region-of-interest setting image 85A1 is received, the illustration image 75 indicating the whole dental arch in planar view is displayed, and the photography region for the dental arch is distinguishably displayed in the illustration image 75. For the example in FIG. 25, the photography region is distinguishably displayed while surrounded by a circle. As described later, in performing the CT photography of the dental arch, the CT photography of a whole or part of the dental arch can be performed by properly setting the size of the photography region.

Thus, the setting of the region of interest is received, and the setting reception processing is performed on other first photography conditions.

In the CT photography mode, the setting of the partial region (size) can be received using the photography region setting image 85D. That is, the photography region setting image 85D is the image in which the image of the numerical vale (such as a diameter and a height) indicating the size of the photography region is added to the illustration (for example a columnar shape) three-dimensionally expressing the shape of the photography region, and the photography region setting image 85D can be recognized as the CT photography region size selection image. When the user touches the photography region setting image 85D, plural photography region setting images 85D1 to 85D8 are displayed instead of the illustration image 72 as illustrated in FIG. 27. At this point, the currently-set region of interest is distinguishably displayed. The photography region setting images 85D1 to 85D8 are plural CT photography region candidate images indicating different CT photography region sizes. That is, the photography region setting images 85D1 to 85D8 are used to set the CT photography regions that differ from one another in one of the diameter, the height, and the photography region shape. When the size of a general jaw or chin with teeth is assumed, relatively narrow region setting screens 85D1 and 85D2 are used to select the local CT photography mode in which about three teeth can be photographed, and relatively wide region setting screens 85D3 to 85D5 are used to select the CT photography mode in which almost of the jaw or chin with teeth can be photographed. In wide region setting screens CT photography modes 85D6 to 85D8, the photography region is formed into a triangular prism shape, and the completely whole jaw or chin with teeth including a molar is selected. Accordingly, the photography region setting image 85D is the mode selection image used to select the modes including the local CT photography mode. When the user touches one of the displayed images 85D1 to 85D8, the setting of the CT photography region size is received. In the case that the reception of the setting of the CT photography region size is not changed, the flow goes to the next processing while the current region of interest is not changed. The upper numerical character described on the right of each illustration indicates the diameter (mm) of the region of interest, and the lower numerical character indicates the height (mm) of the region of interest. The upper and lower jaws can be photographed in the case that the region of interest has the height of 80, the upper or lower jaw can be photographed in the case that the region of interest has the height of 40 or 50, which allows the photograph to be performed while the exposure dose is reduced.

Figure 28:
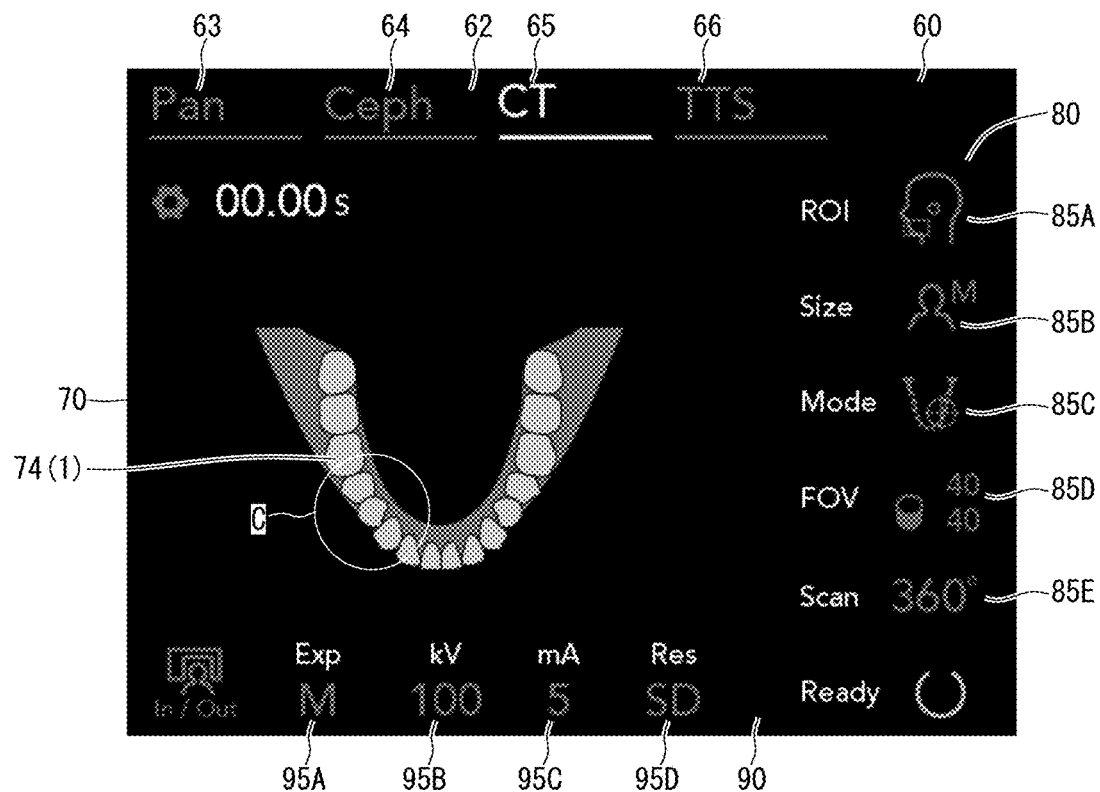
FIG. 28 is a view illustrating a display example when the CT photography mode is selected.

The reception of the selected setting of the photography region also reflects the illustration image 75. That is, the photography region displayed in the illustration image 75 is changed according to the set diameter of the photography region. For example, when the photography region is set to the small diameter, the photography region (surrounded by a circle) displayed in the illustration image 75 becomes small as illustrated in FIG. 28. The size of the dental arch may be changed according to the set diameter of the photography region.

The reception of the selected setting of the photography region also reflects the photography region setting image 85D. That is, the image displayed in the photography region setting image 85D is changed according to the set diameter of the photography region. The displayed image is identical to the image selected from one of the photography region setting images 85D1 to 85D8. The photography region setting images 85D1 to 85D5 indicate different CT photography region sizes, and each of the photography region setting images 85D1 to 85D5 includes a columnar portion having a different size and a numerical value indicating the size (the diameter and the height). When the selection of the local CT photography mode (the selection of each of the images 85D1 to 85D2) is received, the local CT illustration image (one of the images 85D1 to 85D2) indicating the size of the local CT photography region is displayed as the photography region selection image 85D that is of the mode selection image. Therefore, the user can easily understand the size of the local CT photography region in performing the local CT photography.

Figure 29:
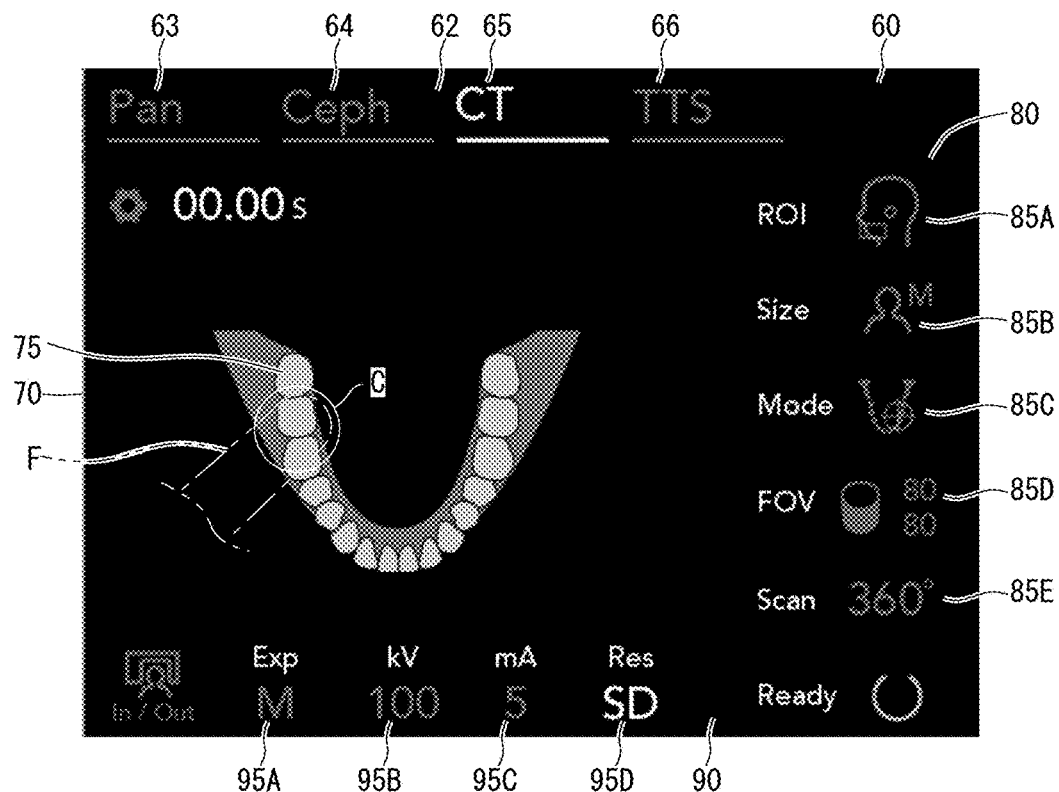
FIG. 29 is a view illustrating a display example when setting of a partial region is received, which is to be photographed using the illustration image.

In the CT photography mode, the setting of the partial region to be photographed can be received using the illustration image 74. For example, as illustrated in FIG. 29, when the user touches one of places of the dental arch with a user's finger F in the region setting illustration image 74 in which the circular shape C indicating the local CT photography region overlaps the illustration image indicating the plan view of the dental arch, the setting of the partial region can be received by moving a circular shape C to the touched position. The circular shape C may be moved relative to the dental arch. Accordingly, for example, the circular shape C is located at a constant position on the display unit 38a, and the position of the dental arch may be moved with respect to the circular shape C and displayed. An instruction to move the circular shape C relative to the dental arch may be issued using two-dimensional position input unit such as a mouse in addition to the direct touch on the display unit 38a, or issued by touching a vertically and horizontally movement screen (cross button screen) displayed on the display unit 38a or by operating a vertically and horizontally movement switch provided separately.

The CT photography region may be set on an already-photographed panoramic image or a two-directional scout image (X-ray images from the front and side directions). In this case, the selection operation is performed using the CT photography mode selection image 85C, which allows the photography region to be set based on the panoramic image or two-directional scout image in addition to the setting of the photography region of the dental arch.

The processing of receiving the setting of the first photography condition is ended when the user ends the reception of the setting of the partial region to be photographed using the illustration image 74. In the case that the reception of the setting of the photography region is not changed, the processing is ended while the current photography region remains.

The description of the second photography condition setting processing will be omitted because the second photography condition setting processing is similar to the setting reception processing in the panoramic photography mode.

<Display Processing in Pseudo-Intraoral Radiography Mode>

Figure 30:
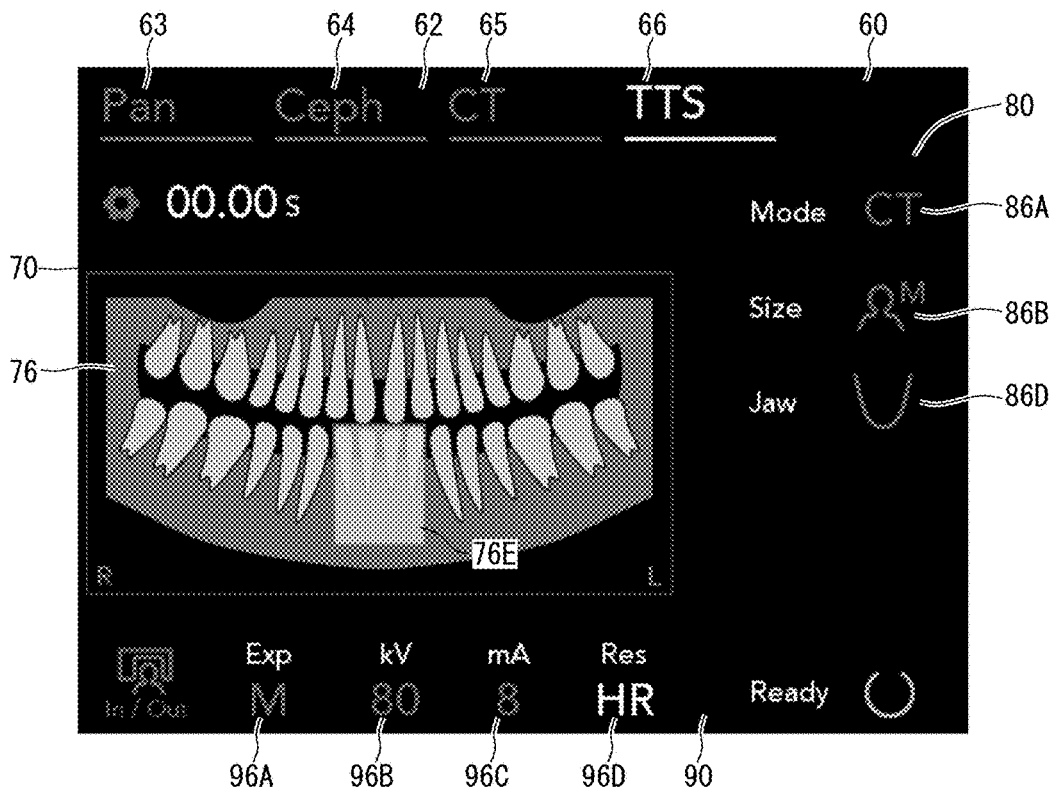
FIG. 30 is a view illustrating a display example when a pseudo-intraoral radiography mode is selected.

FIG. 30 is a view illustrating a display image example of the display unit 38a when the pseudo-intraoral radiography mode is selected. Referring to FIG. 30, the display image example on the display unit 38a includes the photography mode selection region 62, the illustration display region 70, the first photography condition setting region 80, and the second photography condition setting region 90.

The case that the pseudo-intraoral radiography mode selection image 66 is displayed in color (including different shade of color) different from the mode selection images 63, 64, and 65 while being distinguishable from the mode selection images 63, 64, and 65 is illustrated in the photography mode selection region 62.

For the example in FIG. 30, an entire jaw or chin panorama illustration image 76 is displayed as the illustration image corresponding to the pseudo-intraoral radiography mode in the illustration display region 70. The photography region where the teeth are translucent is displayed as a colored region image 76E indicating the selected photography region. Sometimes an illustration image indicating a dental formula image (to be described later) is displayed as the illustration image corresponding to the pseudo-intraoral radiography mode.

A photography condition setting image 86A, a patient size selection image 86B, and a dental arch shape selection image 86D are displayed as the photography condition setting image corresponding to the pseudo-intraoral radiography mode in the first photography condition setting region 80.

An irradiation setting image 96A, a tube voltage setting image 96B, a tube current setting image 96C, and a resolution setting image 96D are displayed as the photography condition setting image corresponding to the pseudo-intraoral radiography mode in the second photography condition setting region 90.

The setting of the photography condition, the selection of the patient size, the setting of the dental arch shape and the like are received using the first photography condition setting region 80. One of plural kinds of photography conditions can be selected in the setting of the photography condition. Each piece of setting reception processing using the photography condition is similar to that in the panoramic photography mode except for a specific content of each setting and the kind of each image.

Processing of receiving the setting of the partial region to be photographed using the entire jaw or chin panorama illustration image 76 can be cited as a recognizable processing example that is one of features in the pseudo-intraoral radiography mode. That is, previously-prepared plural selectable region images 76E overlap the entire jaw or chin panorama illustration image 76. Although a boundary of each region image 76E is added in FIG. 31 for convenience, actually the boundary is not displayed. For example, the plural region images 76E are set to the upper dental arch, and the plural region images 76E are set to the lower dental arch. Each region image 76E is set as an image pursuant to a 10-film method, a 12-film method, and a 14-film method, which are adopted when the X-ray photography is performed in the intraoral method. In the 10-film method, five regions are set while adjacent teeth overlap each other in the lower dental arch, five regions are set while adjacent teeth overlap each other in the upper dental arch, and previously-set predetermined plural teeth are included in each region. Therefore, in the pseudo-intraoral image photographed by the 10-film method, when an identification code is allocated to each region, the photographed teeth (group) can be specified by specifying the identification code. In the 12-film method and the 14-film method, plural regions are set to each of the upper dental arch and the lower dental arch. Similarly, when the identification code is allocated to each region, the photographed teeth (group) can be specified by specifying the identification code.

Figure 31:
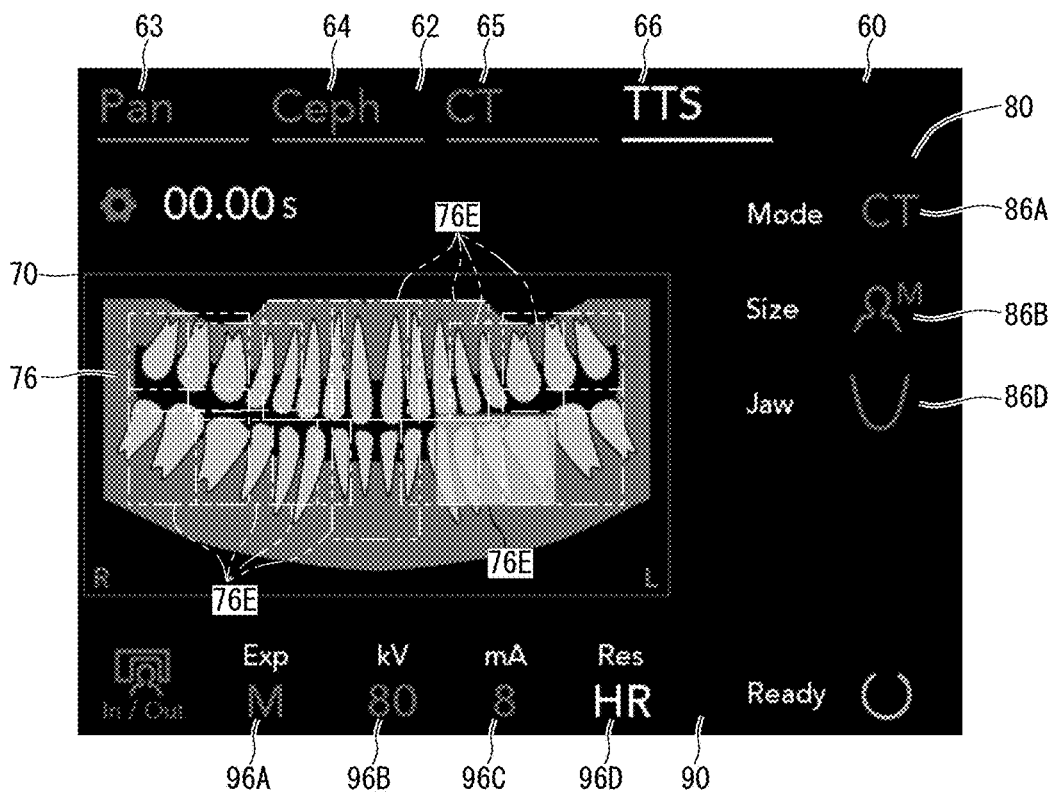
FIG. 31 is a view illustrating a display example when the pseudo-intraoral radiography mode is selected.

In the examples of FIGS. 30 and 31, the region image 76E is set pursuant to the 12-film method. The boundary line defining the region is not displayed in the region that is not selected in FIGS. 30 and 31. The boundary line may be displayed. When the user touches one of the teeth of the entire jaw or chin panorama illustration image 76, the region image 76E corresponding to the photography region including the selected tooth is selectively and distinguishably displayed in the in the illustration image 72. In this case, the selected region image 76E is displayed in color different from other regions. The case that the selected region image 76E is displayed in color different from other regions includes different density. Preferably the selected region image 76E is displayed with a change in hue. Because the non-selected region image 76E is displayed as the illustration image of the non-selected region, a photographing target region is easily understood in the entire jaw or chin panorama illustration image. In FIG. 30, the selected region image 76E in the central region of the lower tooth row is displayed in color different from other images. In FIG. 31, the selected region image 76E in the left region (observer's right) of the lower tooth row is displayed in color different from other images.

Figure 32:
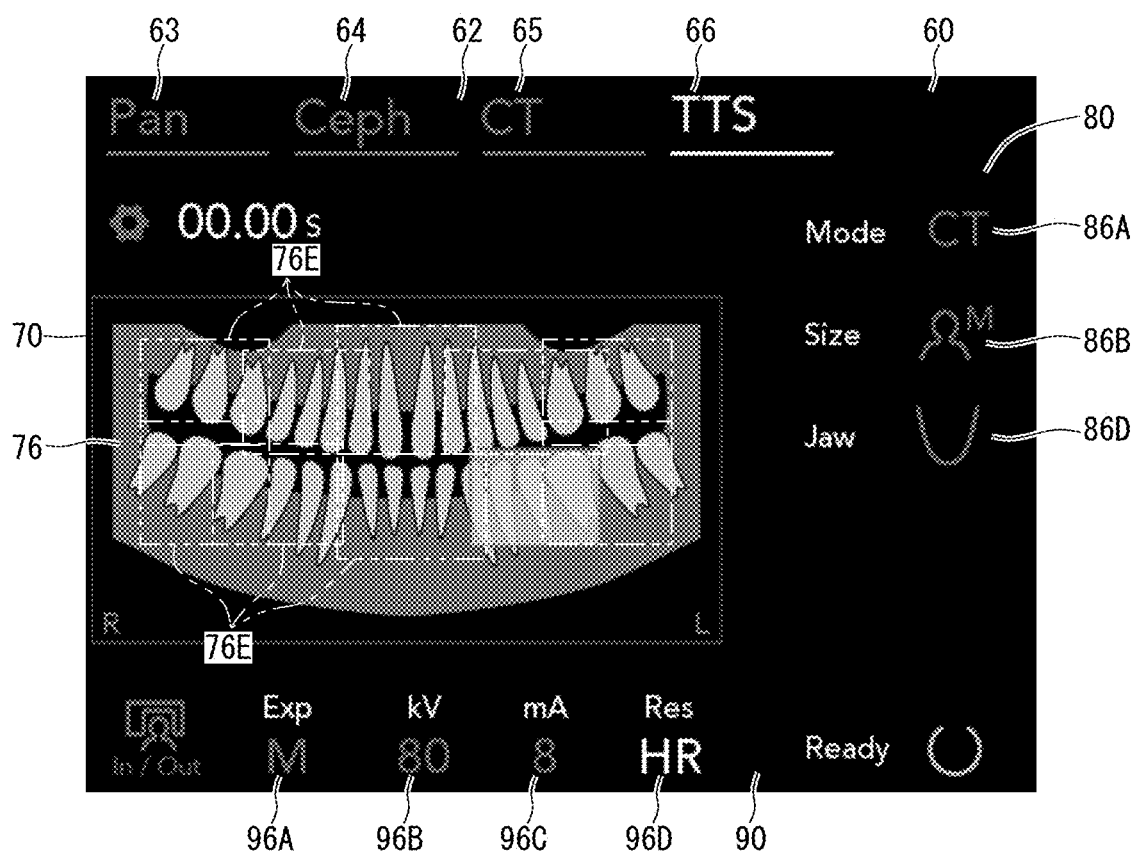
FIG. 32 is a view illustrating another setting example of a region image.

In FIGS. 30 and 31, the 12-film method is described by way of example. For example, in the case that the 10-film method is applied, as illustrated in FIG. 32, five regions are set to the upper tooth row of the entire jaw or chin panorama illustration image 76, and five regions are also set to the lower tooth row. When the user similarly touches one of the teeth of the entire jaw or chin panorama illustration image 76, one of the regions is selected, and the region image 76E corresponding to the selected region is displayed in color different from other images.

The selected region image 76E may be displayed while the images except for the region image 76E are eliminated. In addition to the touch on the display unit 38a by the user, the plural regions may be set by the selection using the mouse. Alternatively, a selection switch is separately provided in the operation panel, and one of the regions may be selected by the operation of the selection switch.

In the preferred embodiment, by way of example, the photographing target region is switched in a unit of block in which the plural teeth are collected by the 10-film method, the 12-film method, and the 14-film method. Alternatively, the photography region may be switched in a unit of tooth.

The pseudo-intraoral radiography region may be set on the already-photographed panoramic image. The region can similarly be set when each region overlaps the panoramic image.

When the user ends the reception of the setting of the partial region to be photographed using the illustration image 76, the processing of receiving the setting of the first photography condition is ended. In the case that the reception of the setting of the photography region is not changed, the flow goes to the next processing while the current photography region is not changed.

The description of the second photography condition setting processing will be omitted because the second photography condition setting processing is similar to the setting reception processing in the panoramic photography mode.

<Modifications Related to Region Designation>

In the preferred embodiment, the pseudo-intraoral radiograph region is set using the entire jaw or chin panorama illustration image 76. Alternatively, it is also conceivable that the region is set using the dental formula image as described below.

Figure 33:
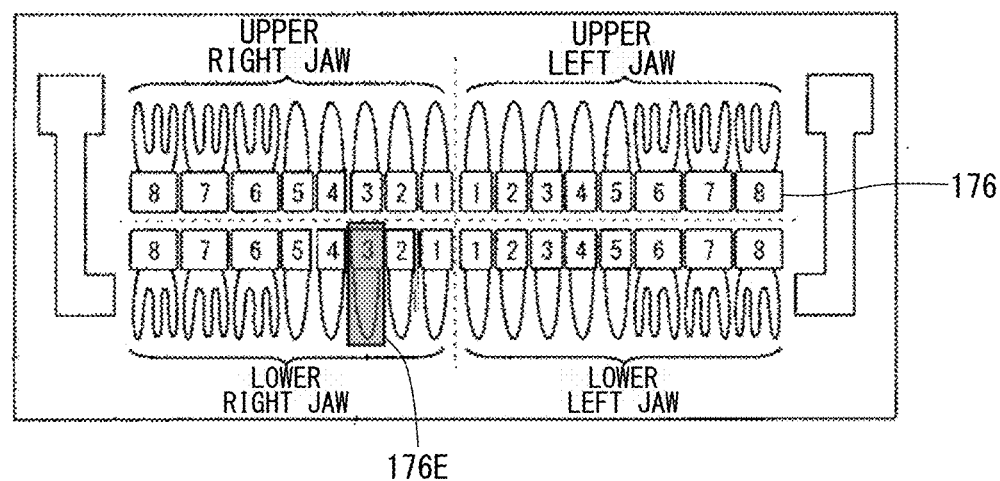
FIG. 33 is a view illustrating a display example when a region is set using a dental formula image.
Figure 34:
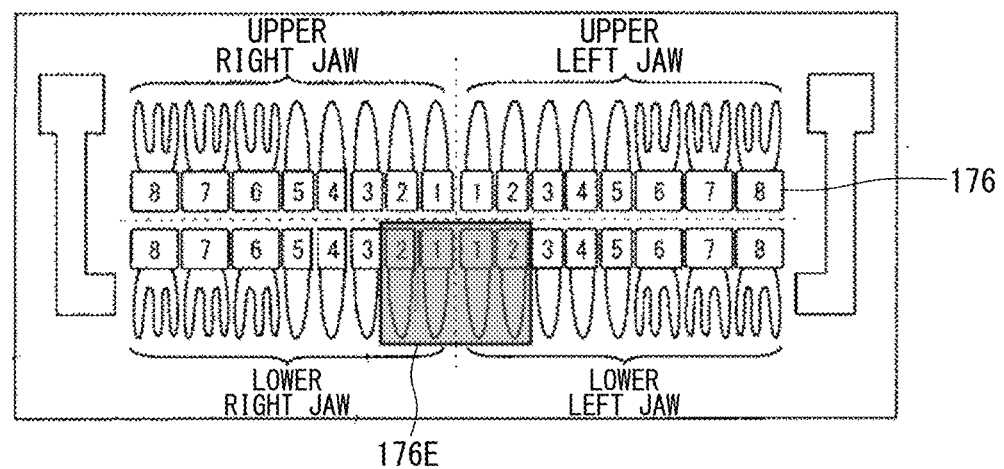
FIG. 34 is a view illustrating a display example when the region is set using the dental formula image.

In the example of FIGS. 33 and 34, a dental formula image 176 is displayed as the illustration image corresponding to the pseudo-intraoral radiography mode. For the example in FIG. 33, the dental formula image 176 includes the illustration image in which the dental formulas corresponding to the teeth are arrayed according to arrangement of the teeth. The dental formula may be a Japanese dental formula, an FDI (Two-digit system) dental formula, or an American (Universal system) dental formula. FIGS. 32 and 33 illustrate the Japanese dental formula.

FIG. 33 illustrates the case that the photography region is designated in a unit of tooth using the dental formula image. That is, in the dental formula image 176, the photography region is set in a unit of tooth, and the photography region is designated when the user designates the dental formula corresponding to one of the teeth. The user touches the dental formula designation place in the dental formula image 176, whereby the photography region may be designated. The photography region may be designated using the mouse, or the photography region may be designated by directly designating the dental formula using a numeric keypad. The designated photography region 176E is displayed in the visually distinguishable manner. In FIG. 33, the photography region 176E is displayed in color different from other images.

FIG. 34 illustrates the case that the photography region is designated in a unit of plural teeth. That is, in the dental formula image 176, the photography region is set in a unit of block including plural tooth numbers. As described above, the block may be set in a unit of the block used in the pseudo-intraoral radiograph of the 10-film method, 12-film method, and 14-film method, or set in a unit of another block. The user touches the dental formula designation place in the dental formula image 176 as described above, whereby the photography region may be designated. The photography region may be designated using the mouse, or the photography region may be designated by directly designating the dental formula using a numeric keypad. The designated photography region 176E is displayed in the visually distinguishable manner.

Figure 35:
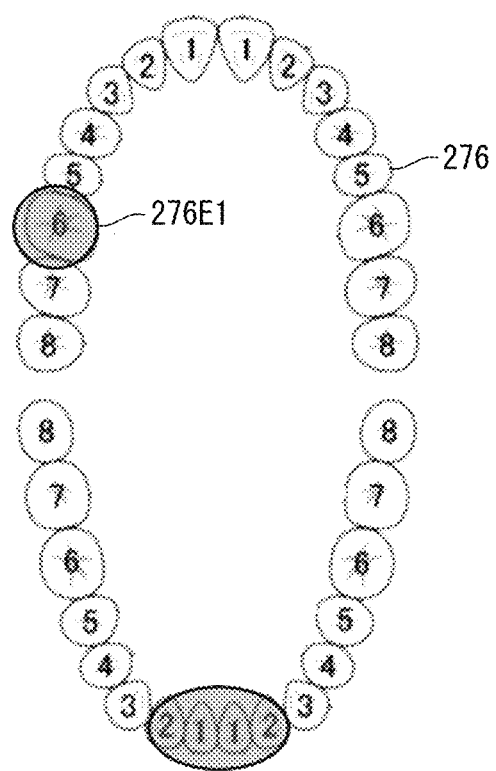
FIG. 35 is a view illustrating a display example when the region is set using the dental formula image.

As illustrated in FIG. 35, even in a dental formula image 276 in which the upper and lower dental formulas are circularly disposed according to the arrangement of the upper and lower tooth rows, similarly a photography region 276E1 can be designated in a unit of tooth number, and a photography region 276E2 can be designated in a unit of block including plural tooth numbers.

<Application of Region Designation of Local CT Photography>

The region designation processing applied in performing the pseudo-intraoral radiograph can also be used to designate the local photography region of the photographing target in performing the local CT photography.

Particularly, the region setting processing using the dental formula images 176 and 276 and the processing of visibly displaying the designated region, which are performed in the pseudo-intraoral radiograph as illustrated in FIGS. 33 to 35, can similarly applied in performing the local CT photography.

<Photographed Image Example>

Preferably the X-ray image obtained by photographing with the medical X-ray photography apparatus 10 is displayed while at least upper, lower, right, and left symbols overlap the X-ray image.

For example, in an example of FIG. 36, a symbol "U" indicating up overlaps a pseudo-intraoral X-ray image 300 obtained by the photography of the photographing target designated in the pseudo-intraoral radiography mode, a symbol "B" indicating below overlaps the pseudo-intraoral X-ray image 300, a symbol "R" indicating right (observer's left) overlaps the pseudo-intraoral X-ray image 300, and a symbol "L" indicating left (observer's right) overlaps the pseudo-intraoral X-ray image 300. The upper, lower, right, and left symbols may overlap the inside of the X-ray image, or the outside of the X-ray image. A type of the photography method such as the 10-film method, the 12-film method, and the 14-film method and a dental formula number 302 (for example, "12, 11, 21, 22" for the FDI (Two-digit system), and the tooth number or direction may be described pursuant to any one of the Japanese and American display systems) may overlap the pseudo-intraoral X-ray image 300. Alternatively, the pseudo-intraoral X-ray image 300 may be stored while linked a block number in the photography mode. The display of the dental formula number, the direction, or the block number does not overlap the pseudo-intraoral X-ray image 300, but each image may be stored in a template, which is correlated with the pseudo-intraoral X-ray image 300 in the storage and separately prepared according to an anatomical arrangement. When each image is stored while linked to the template prepared according to the anatomical arrangement, not only the pseudo-intraoral X-ray image, but also the partial panorama image, the partial cephalo image, and the local CT photography image may be used in the method for easily calling or storing each image. The display of the dental formula number, the direction, or the block number and the storage of each image linked to the template are not limited to the pseudo-intraoral radiography, but may be used in the partial panoramic photography and the local CT photography. The display of the direction may be used in the partial cephalo photography.

The image that is displayed while the upper, lower, right, and left symbols overlap the image may be the panoramic photography image, the cephalo photography image, and the CT image.

The dental formula number, the direction, or the block number may be displayed while overlapping the partial panorama image or the local CT photography image.

The photographed image example is not limited to the medical X-ray photography apparatus that performs the above-described pieces of processing, but can be applied to the various medical X-ray photography apparatuses As described above, in the preferred embodiment, when the user operates one of the plural photography mode selection images 63, 64, 65, and 66, the operation receiver such as the touch detector 38b receives the selection operation, one of the plural photography mode selection images 63, 64, 65, and 66 is displayed in the visually distinguishable manner in the photography mode selection region 62 according to the selection operation, and the illustration image 72 is displayed in the illustration display region 70 according to the selection operation. Therefore, the user easily recognizes the selected photography mode before and after the selection operation, and the user easily sets the photography mode. After the selection operation, the user easily sets the photography region using the illustration image 72 displayed according to the selection operation in the display unit 38a.

When at least two of the panoramic photography, the cephalo photography, the CT photography, and the pseudo-intraoral radiograph are included as the photography mode to which the display processing is applied, the photography mode and the photography region are easily set during the selection of the panoramic photography, the cephalo photography, the CT photography, and the pseudo-intraoral radiograph.

When the selection operation for one of the plural photography mode selection images 63, 64, 65, and 66 is received, the photography condition setting image (such as the region-of-interest setting image 83A, the patient size selection image 83B, the projection setting image 83C, and the dental arch shape selection image 83D for the panoramic photography mode) is displayed in the first photography condition setting region 80 according to the selection operation. Therefore, the user can easily set the detailed photography condition corresponding to the photography mode.

Similarly, the user can easily set the detailed photography condition corresponding to the photography mode using the first photography condition setting region 80.

When the panoramic photography mode is selected, the illustration image 73 indicating the entire jaw or chin panorama or the illustration image 73a indicating the plan view of the dental arch is displayed in the illustration display region 70. Therefore, the user can easily set the photography region using the illustration image 73 indicating the entire jaw or chin panorama or the illustration image 73a indicating the plan view of the dental arch.

The user easily sets the photography region using the entire jaw or chin panorama illustration image 73. Because the selected photography region is displayed in the visually distinguishable manner in the entire jaw or chin panorama illustration image 73, the user easily sets the photography region while recognizing the selected photography region.

When the panoramic photography mode is selected, at least one of the patient size selection image 83B and the image indicating the jaw or chin shape of the photographing target is displayed as the image indicating the patient size in the first photography condition setting region 80, so that the user can easily set the detailed photography condition of the panoramic photography mode.

Because the dental arch shape selection image 83D is displayed as the photography condition setting image corresponding to the panoramic photography mode in the first photography condition setting region 80, the standard dental arch illustration image 83D1 indicating the standard dental arch and the protraction dental arch illustration image 83D2 indicating the protraction dental arch are displayed on the display unit 38a when the user selects the dental arch shape selection image 83D. When the user selects the standard dental arch illustration image 83D1 or the protraction dental arch illustration image 83D2 indicating the protraction dental arch, the illustration image is displayed in the illustration display region 70 according to the selection operation. Therefore, the user can easily change the illustration image displayed in the illustration display region 70.

When the user operates the patient size selection image 83B displayed in the first photography condition setting region 80 in each photography mode, the plural patient size selection images 83B1 to 83B4 are displayed. The user can easily set the patient size by selectively operating the plural patient size selection images 83B1 to 83B4.

The tube current setting image 93C and the tube voltage setting image 93B are displayed in the second photography condition setting region 90, the tube current or tube voltage adjustment image is displayed by the selection operation, so that the user can easily adjust the tube current and tube voltage while easily recognizing the tube current and tube voltage.

When the cephalo photography mode is selected, the illustration image 74 or 74(1) indicating the front or side face of the external head shape is displayed in the illustration display region 70. Therefore, the user easily sets the photography region using the illustration image 74 or 74(1) indicating the front or side face of the external head shape.

The illustration image 74 or 74(1) indicating the front or side face of the external head shape is divided into the plural regions while being able to be divided as the partial cephalo photography region, and the selection operation for at least one of the plural regions is received. Therefore, in the illustration image 74 or 74(1) indicating the front or side face of the external head shape, the selected photography region is displayed in the visually distinguishable manner, so that the user can easily designate the partial cephalo photography region.

When the CT photography mode is selected, the illustration image 75 indicating the plan view of the dental arch is displayed in the illustration display region 70. Therefore, the user easily sets the photography region using the illustration image 75 indicating the plan view of the dental arch.

The photography region setting image 85D that is of the CT photography region size selection image is displayed as the photography condition setting image corresponding to the CT photography mode in the first photography condition setting region 80. When the user selects the photography region setting image 85D, the photography region setting images 85D1 to 85D8 having different CT photography regions are displayed. The user can easily change the CT photography region size when touching one of the displayed images 85D1 to 85D8.

The user can easily change the region where the local CT photography is performed while checking the position of the circular shape indicating the local CT photography region of the illustration image 75 indicating the plan view of the dental arch.

When the pseudo-intraoral radiography mode is selected, the entire jaw or chin panorama illustration image 76 is displayed in the illustration display region. Therefore, the user easily sets the photography region using the entire jaw or chin panorama illustration image 76. Because the selected photography region is displayed in the visually distinguishable manner in the entire jaw or chin panorama illustration image 76, the user more easily sets the photography region while recognizing the selected photography region.

When the pseudo-intraoral radiography mode is selected, the dental formula image 176 or 276 is displayed in the illustration display region such that the photography region can be selected in each tooth number or each block including the plural tooth numbers using the dental formula image. At this point, the user easily sets the photography region in each tooth number or each block including the plural tooth numbers using the dental formula image. Because the selected photography region is displayed in the visually distinguishable manner in the dental formula image, the user more easily sets the photography region while recognizing the selected photography region.

The upper, lower, right, and left symbols overlap the actually-photographed X-ray image, which allows the user to easily recognize the direction of the X-ray image.

The configurations described in the preferred embodiment and modifications can properly be combined with each other unless the configurations are inconsistent with each other. Specifically, the combination machine having the panoramic photography function, the cephalo photography function, the CT photography function, and the pseudo-intraoral radiography function is mainly described in the preferred embodiment. However, the X-ray photography apparatus having at least one of the panoramic photography function, the cephalo photography function, the CT photography function, and the pseudo-intraoral radiography function is included in the scope of the present invention.

While the invention has been shown and described in detail, the foregoing description is in all aspects illustrative and not restrictive. It is therefore understood that numerous modifications and variations can be devised without departing from the scope of the invention.

The invention claimed is:

1. A display for a medical X-ray photography apparatus, the display comprising:
   a display panel including a photography mode selection region where a plurality of photography mode selection images corresponding to a plurality of X-ray photography modes are displayed, the plurality of X-ray photography modes being at least two of a panoramic photography mode, a CT photography mode, a cephalo photography mode, and a pseudo-intraoral radiography mode;
   an interface that receives a selection operation to select one of the photography mode selection images displayed on the display panel;
   a processor that performs display processing of the selected photography mode selection image displayed on the display panel in response to the selection operation received through the interface; and the display panel including an illustration display region where an illustration corresponding to the selected photography mode selection image is displayed, the display panel also including a photography condition setting region where a photography condition setting image corresponding to the plurality of X-ray photography modes is displayed;

wherein, when the selection operation is received, the selected photography mode selection image is displayed in a visually distinguishable manner from another, unselected photography mode selection image in the photography mode selection region, the illustration corresponding to the selected photography mode selection image is displayed in the illustration display region, a tube current setting image including tube current display and a tube voltage setting image including tube voltage display are displayed in the photography condition setting region, and a tube current adjustment image or tube voltage adjustment image is displayed by selection operation for the tube current setting image or the tube voltage setting image.

2. The display for a medical X-ray photography apparatus according to claim 1, wherein the plurality of photography mode selection images include at least two of: a panoramic photography mode selection image corresponding to panoramic photography, a cephalo photography mode selection image corresponding to cephalo photography, a CT photography mode selection image corresponding to CT photography, and a pseudo-intraoral radiography mode selection image corresponding to pseudo-intraoral radiograph.

3. The display for a medical X-ray photography apparatus according to claim 1, wherein an illustration indicating an entire chin panorama or a plan view of a dental arch is displayed in the illustration display region as an illustration corresponding to a panoramic photography mode as said illustration.

4. The display for a medical X-ray photography apparatus according to claim 1, wherein an illustration of an entire chin panorama is displayed in the illustration display region as an illustration corresponding to a panoramic photography mode as said illustration, and when a photography region selection operation based on the illustration of the entire chin panorama is received, a photography region of a selected partial panorama is displayed in a visually distinguishable manner in the illustration of the entire chin panorama.

5. The display for a medical X-ray photography apparatus according to claim 1, wherein an illustration indicating a front view or a side view of an external head shape is displayed in the illustration display region as the illustration corresponding to a cephalo photography mode.

6. The display for a medical X-ray photography apparatus according to claim 5, wherein the illustration indicating the front view or the side view of the external head shape is divided into a plurality of regions while being able to be divided as a partial cephalo photography region, and when a selection operation for one of the plurality of regions is received, a selected photography region is displayed in a visually distinguishable manner in the illustration indicating the front view or the side view of the external head shape.

7. The display for a medical X-ray photography apparatus according to claim 1, wherein an illustration image indicating a plan view of a dental arch is displayed in the illustration display region as an illustration corresponding to a CT photography mode as said illustration.

8. The display for a medical X-ray photography apparatus according to claim 1, wherein an illustration of an entire chin panorama is displayed in the illustration display region as an illustration corresponding to a pseudo-intraoral radiography mode as said illustration, and when a photography region selection operation based on the illustration of the entire chin panorama is received, a selected photography region is displayed in a visually distinguishable manner in the illustration of the entire chin panorama.

9. The display for a medical X-ray photography apparatus according to claim 1, wherein a dental formula image is displayed in the illustration display region as an illustration corresponding to a pseudo-intraoral radiography mode as said illustration such that a photography region can be selected in each tooth number or each block including a plurality of tooth numbers, and when a photography region selection operation based on the dental formula image is received, a selected photography region is displayed in a visually distinguishable manner in the dental formula image.

10. The display for a medical X-ray photography apparatus according to claim 1, wherein the display panel includes another photography condition setting region where a photography condition setting image corresponding to the plurality of photography modes is displayed, and when the selection operation is received with respect to one of the plurality of photography mode selection images, the photography condition setting image corresponding to the selection operation is displayed in the another photography condition setting region.

11. The display for a medical X-ray photography apparatus according to claim 10, wherein an image indicating a patient size or an image indicating a chin shape is displayed in the first photography condition setting region as the photography condition setting image corresponding to a panoramic photography mode.

12. The display for a medical X-ray photography apparatus according to claim 10, wherein a patient dental arch shape selection image is displayed in the another photography condition setting region as the photography condition setting image corresponding to a panoramic photography mode, and when a selection operation for the patient dental arch shape selection image is received, a standard dental arch illustration image indicating a standard dental arch and a protraction dental arch illustration image indicating a protraction dental arch are displayed in the display panel.

13. The display for a medical X-ray photography apparatus according to claim 10, wherein a CT photography region size selection image as the photography condition setting image corresponding to a CT photography mode is displayed in the another photography condition setting region, and when a selection operation for the CT photography region size selection image is received, a plurality of CT photography region size candidate images indicating CT photography region sizes different from each other are displayed in the display panel.

14. The display for a medical X-ray photography apparatus according to claim 10, wherein a photography region setting image is displayed in the another photography condition setting region as the photography condition setting image corresponding to a CT photography mode in order to select and designate a mode of CT photography region including a local CT photography mode, and when a selection of the local CT photography mode is received, a local CT illustration image indicating a size of a local CT photography region is displayed as the photography condition setting image.

15. The display for a medical X-ray photography apparatus according to claim 14, wherein, when the selection of the local CT photography mode is received, a region setting illustration image in which a circular shape indicating the local CT photography region is superposed on an illustration image of a plan view of a dental arch is displayed as said illustration image in the illustration display region, and when relative movement of the circular shape indicating the local CT photography region with respect to the illustration image of the plan view of the dental arch is received, a position of the circular shape indicating the local CT photography region is changed with respect to the illustration image of the plan view of the dental arch according to the relative movement.

16. The display for a medical X-ray photography apparatus according to claim 14, wherein a dental formula image is displayed in the illustration display region as the illustration image corresponding to the local CT photography mode such that a photography region can be selected in each tooth number or each block including a plurality of tooth numbers, and when a photography region selection operation based on the dental formula image is received, a selected photography region is displayed in a visually distinguishable manner in the dental formula image.

17. The display for a medical X-ray photography apparatus according to claim 10, wherein a photography region selection image is displayed in the another photography condition setting region as the photography condition setting image corresponding to a cephalo photography mode, and when a selection operation for the photography region selection image is received, a head front external form illustration image indicating a head front external form and a head side illustration image indicating a head side external form are displayed in the display panel.

18. The display for a medical X-ray photography apparatus according to claim 10, wherein a patient size selection image is displayed in the another photography condition setting region, and when a selection operation for the patient size selection image is received, a plurality of patient size display illustration images indicating upper body external forms having different sizes are displayed in the display panel.

19. The display for a medical X-ray photography apparatus according to claim 1, wherein an X-ray image photographed in one of the plurality of X-ray photography modes is displayed in the display panel while a symbol indicating one of an up, a down, a right, or a left direction is superposed on the X-ray image.

20. A medical X-ray photography apparatus comprising the display for medical X-ray photography apparatus according to claim 1.

21. A display method in a display for a medical X-ray photography apparatus, the display method comprising the steps of:

(a) displaying a plurality of photography mode selection images corresponding to a plurality of X-ray photography modes in a photography mode selection region, the plurality of X-ray photography modes being at least two of a panoramic photography mode, a CT photography mode, a cephalo photography mode, and a pseudo-intraoral radiography mode;

(b) receiving a selection operation for one of the plurality of photography mode selection images;

(c) displaying one photography mode selection image in the plurality of photography mode selection images in a visually distinguishable manner from another, unselected photography mode selection image in the photography mode selection region according to the selection operation when the selection operation in step (b) is received;

(d) displaying an illustration image in an illustration display region according to the selection operation when the selection operation in step (b) is received; and (e) displaying a tube current setting image including tube current display and a tube voltage setting image including tube voltage display in a photography condition setting region and displaying a tube current adjustment image or a tube voltage adjustment image by selection operation for the tube current setting image or the tube voltage setting image when the selection operation in step (b) is received.

22. The display method in the display for the medical X-ray photography apparatus according to claim 21, wherein at least two of a panoramic photography mode selection image corresponding to panoramic photography, a cephalo photography mode selection image corresponding to cephalo photography, a CT photography mode selection image corresponding to CT photography, and a pseudo-intraoral radiography mode selection image corresponding to pseudo-intraoral radiograph are displayed as the plurality of photography mode selection images in step (a).

23. The display method in the display for the medical X-ray photography apparatus according to claim 21, further comprising the step of displaying a photography condition setting image in another photography condition setting region according to the selection operation when the selection operation in step (b) is received.

* * * * *